US012667332B2

(12) United States Patent
Katagiri

(10) Patent No.: US 12,667,332 B2
(45) Date of Patent: Jun. 30, 2026

(54) ULTRASONIC DIAGNOSTIC DEVICE WITH HINGE AND HANDLE MECHANISMS TO LOCK THE DEVICE ONTO A CART

(71) Applicant: FUJIFILM Corporation, Tokyo (JP)

(72) Inventor: Kengo Katagiri, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/080,941

(22) Filed: Mar. 17, 2025

(65) Prior Publication Data

US 2025/0295387 A1 Sep. 25, 2025

(30) Foreign Application Priority Data

Mar. 22, 2024 (JP) ................................. 2024-045890

(51) Int. Cl.
*A61B 8/00* (2006.01)
(52) U.S. Cl.
CPC ................................. *A61B 8/4427* (2013.01)

(58) Field of Classification Search
CPC ... A61B 8/4427; A61B 8/4433; A61B 8/4405; A61B 8/44
See application file for complete search history.

(56) References Cited

FOREIGN PATENT DOCUMENTS

JP        2008023007        2/2008
JP        2015205007        11/2015

*Primary Examiner* — Serkan Akar
(74) *Attorney, Agent, or Firm* — JCIPRNET

(57) ABSTRACT

In a case where a main body unit is transported by gripping a grip of a handle, the main body unit is protected. In addition, cleanliness of the grip is maintained. A main body has a hinge mechanism. A handle is connected to the hinge mechanism. The hinge mechanism has a handle locking mechanism. The handle locking mechanism locks the handle at a first rotation angle or a second rotation angle. In a case where the handle is used as a stand, a grip does not come into contact with a placement surface.

5 Claims, 25 Drawing Sheets

FIG. 13

INSTALL FRONT PORTION OF MAIN BODY
(SLIDE RESTRICTED STATE, HANDLE LOCKED STATE) — S10

START DOWNWARD MOVEMENT OF MAIN BODY — S12

PUSH KNOB — S14

RELEASE HANDLE LOCK — S16

PUSH BUTTON — S18

RELEASE SLIDE RESTRICTION — S20

COMPLETE INSTALLATION OF MAIN BODY — S22

TILT HANDLE — S24

OPERATE HOOK MEMBER — S26

HANDLE FIXED STATE
MAIN BODY FIXED STATE — S28

USE ULTRASOUND
DIAGNOSTIC APPARATUS — S30

END USE OF ULTRASOUND DIAGNOSTIC APPARATUS — S32

OPERATE LOCK RELEASE BUTTON — S34

RELEASE HANDLE FIXING RELEASE MAIN BODY FIXING — S36

START LIFTING OF HANDLE — S38

RISING OF BUTTON — S44

PROTRUDING OF KNOB — S40

RESTRICT SLIDING — S46

LOCK HANDLE — S42

DETACH MAIN BODY UNIT FROM CART (SLIDE RESTRICTED STATE, HANDLE LOCKED STATE) — S48

1

ULTRASONIC DIAGNOSTIC DEVICE WITH HINGE AND HANDLE MECHANISMS TO LOCK THE DEVICE ONTO A CART

CROSS-REFERENCE TO RELATED APPLICATION

This application claims the priority benefit of Japan application serial no. 2024-045890, filed on Mar. 22, 2024. The entirety of the above-mentioned patent application is hereby incorporated by reference herein and made a part of this specification.

BACKGROUND OF THE INVENTION

1. Field of the Invention

The present disclosure relates to an ultrasonic diagnostic device and particularly to an ultrasonic diagnostic device having a handle.

2. Description of the Related Art

An ultrasonic diagnostic device that can be carried by hand is used in many medical institutions. Such a portable ultrasonic diagnostic device is composed of a main body unit and an ultrasound probe. The main body unit has a form of, for example, a notebook personal computer (PC). In this case, the main body unit is composed of a main body that generates an ultrasound image and a display that displays the ultrasound image. The portable ultrasonic diagnostic device is generally used in a state of being installed on a dedicated cart or on a general-purpose table. An ultrasound diagnostic apparatus is composed of the portable ultrasonic diagnostic device and the cart on which the ultrasonic diagnostic device is installed. The portable ultrasonic diagnostic device itself may be called the ultrasound diagnostic apparatus.

JP 2008-23007A discloses an ultrasound diagnostic apparatus composed of a portable ultrasonic diagnostic device and a cart. A main body of the ultrasonic diagnostic device has a handle. JP 2008-23007A does not describe a mechanism that fixes a handle to the main body.

JP 2015-205007A discloses an ultrasonic diagnostic device that has a handle. The handle functions as a cover that covers a rear portion of the ultrasonic diagnostic device and also functions as a stand of the ultrasonic diagnostic device. In the paragraph of 0045 of JP 2015-205007A, a mechanism that locks the handle in a case where the handle functions as the cover is mentioned. JP 2015-205007A does not describe lock of the handle in a case where the ultrasonic diagnostic device is transported.

SUMMARY OF THE INVENTION

In a case where the main body unit is transported while gripping a grip of the handle and suspending the main body unit (the main body and the display), the main body unit is likely to come into contact with or collide with another thing (another medical device, a user himself/herself, or the like) when a free change in a rotation angle of the handle is allowed. In particular, in a case where an inclined angle of the main body unit with respect to a vertical line is large (for example, in a case where an inclined angle of the main body exceeds 5 degrees or 10 degrees) in a suspended state, such a problem is likely to occur. In the suspended state, it is desirable to prevent the free change in the rotation angle of the handle while reducing the inclined angle of the main body unit.

In a case where the ultrasonic diagnostic device is placed on a general-purpose table and the ultrasonic diagnostic device is used, it is desirable that the handle functions as the stand in order to incline the main body unit of the ultrasonic diagnostic device. In this case, in a case where the grip in the handle comes into contact with a table surface, the grip is likely to be contaminated.

The present disclosure protects a main body unit in a case where the main body unit is transported by gripping a grip of a handle.

According to an aspect of the present disclosure, there is provided an ultrasonic diagnostic device comprising a main body unit that has a main body which generates an ultrasound image and a display which displays the ultrasound image, a hinge mechanism that is provided at the main body, and a handle that has two arms which are connected to the hinge mechanism and a grip which is connected to the two arms, in which the hinge mechanism includes a handle locking mechanism that locks the handle at a first rotation angle in a case where the main body unit is transported by gripping the grip.

With the present disclosure, the main body unit can be protected in a case where the main body unit is transported by gripping the grip in the handle.

BRIEF DESCRIPTION OF THE DRAWINGS

FIG. 13 is a view showing a completed state in the main body installation process.

DESCRIPTION OF THE PREFERRED EMBODIMENTS

Figure 1:
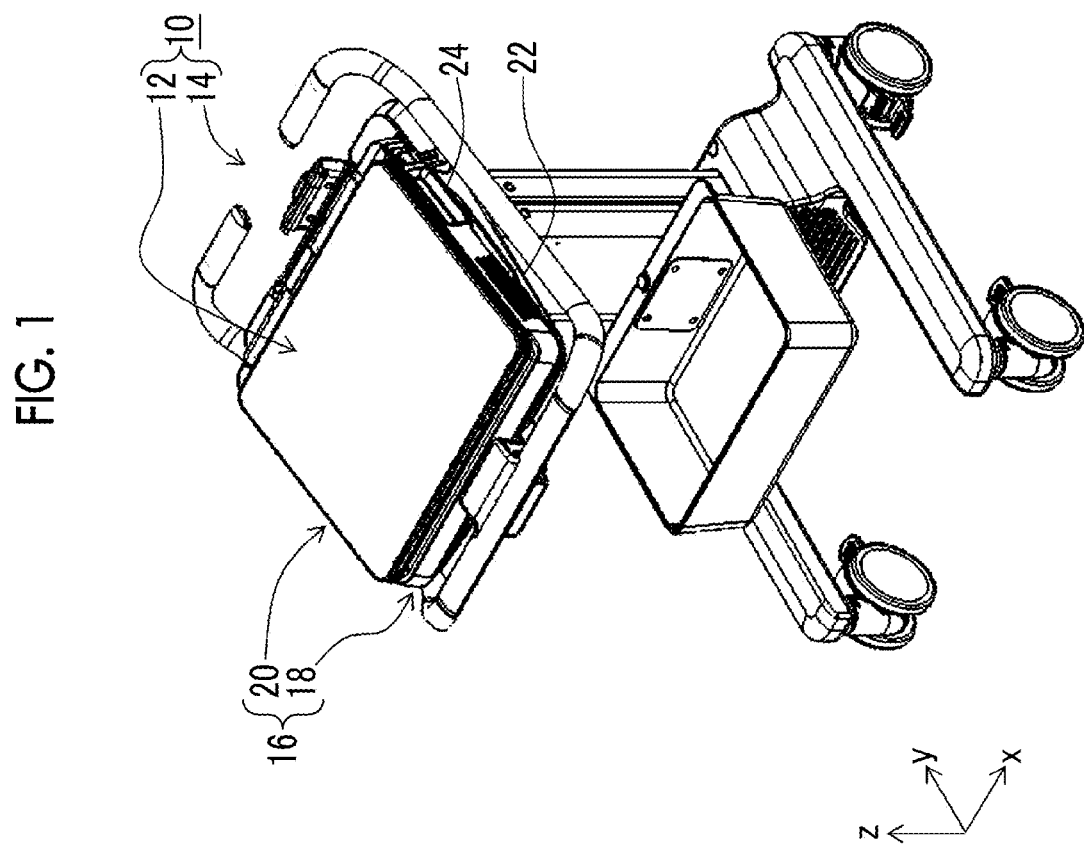
FIG. 1 is a first perspective view showing an ultrasound diagnostic apparatus according to an embodiment.

Hereinafter, an embodiment will be described with reference to the drawings.

(1) Outline of Embodiment

An ultrasonic diagnostic device according to the embodiment has a main body unit, a hinge mechanism, and a handle. The main body unit has a main body that generates an ultrasound image and a display that displays the ultrasound image. The hinge mechanism is provided in the main body. The handle has two arms connected to the hinge mechanism and a grip connected to the two arms. The hinge mechanism includes a handle locking mechanism that locks the handle at a first rotation angle in a case where the main body unit is transported by gripping the grip.

With the above configuration, in a case where the main body unit is suspended and transported, a posture of the main body unit is stabilized. Accordingly, a probability in which the main body unit collides with another member can be reduced. Since the hinge mechanism has the handle locking mechanism, the handle can be reliably locked.

In the embodiment, a hinge mechanism is provided at a rear portion of the main body. In a suspend state of the main body unit, the rear portion of the main body unit is positioned above, and a front portion of the main body unit is positioned below. The handle is indirectly connected to the main body via the hinge mechanism.

In the embodiment, in a case where the handle is used as a stand, the handle locking mechanism locks the handle at a second rotation angle different from the first rotation angle. With this configuration, in a case where the handle is used as the stand, inadvertent rotation of the handle, that is, an inadvertent posture change of the handle can be prevented. For example, the handle locking mechanism has one or a plurality of cams for setting each locking angle to the first rotation angle and the second rotation angle.

In the embodiment, each of the two arms has a bent portion. The second rotation angle is an angle at which the two bent portions of the two arms come into contact with a placement surface on which the main body unit is placed and the grip is separated apart from the placement surface. With this configuration, since the grip does not come into contact with the placement surface, cleanliness of the grip can be maintained.

In the embodiment, the hinge mechanism is provided at a rear end part of the main body. Each of the two arms has a first portion connected to the hinge mechanism, a second portion connected to the grip, and a bent portion between the first portion and the second portion. In a case where the rotation angle of the handle is the first rotation angle, the two first portions of the two arms are near or come into contact with a rear surface of the main body. With this configuration, during transport of the main body unit, the two first portions of the handle are less likely to interfere.

In the embodiment, in a case where the handle is used as a stand, the handle locking mechanism locks the handle at a second rotation angle different from the first rotation angle. In a case where the handle is used as the stand, the grip is positioned in front of the two bent portions of the two arms. With this configuration, the amount of the handle protruding from a space below the main body can be reduced or can be made zero.

In the embodiment, in a case where the handle is used as the stand, the two bent portions come into contact with the placement surface on which the main body unit is placed, and a gap is generated between the grip and the placement surface. With this configuration, cleanliness of the grip can be maintained.

In the embodiment, the main body unit has centroid. In a case where the grip is gripped and the main body unit is suspended, a vertical line passing through the centroid passes through an inside of the grip. With this configuration, during transport of the main body unit, the inclined angle of the main body unit is small, so that a probability in which the main body unit collides with another member can be reduced.

In the embodiment, the handle locking mechanism has a knob that is operated by the user in a case of unlocking the rotation angle. With this configuration, it is easy to unlock the rotation angle.

(2) Details of Embodiment

(2-1) Ultrasound Diagnostic Apparatus

FIG. 1 shows an ultrasound diagnostic apparatus 10 according to the embodiment. The ultrasound diagnostic apparatus 10 is a medical apparatus used in a case where ultrasound examination is performed in a medical institution. The ultrasound diagnostic apparatus 10 is composed of an ultrasonic diagnostic device 12 and a cart 14. The ultrasonic diagnostic device 12 is composed of a main body unit 16 and an ultrasound probe (not shown). The main body unit 16 has a form of a notebook PC. Specifically, the main body unit 16 is composed of a main body 18 and a display 20. In FIG. 1, an x-direction is a right-left direction (width direction), a y-direction is a front-rear direction (depth direction), and a z-direction is an up-down direction (height direction). In general, the user is positioned on a front side of the main body unit 16 and operates the main body unit 16.

The cart 14 has a table 22 on which the main body unit 16 is placed. The table 22 is a member that supports the main body unit 16. The table 22 is slightly inclined with respect to an xy plane. An inclined angle thereof is, for example, within a range of 8 to 12 degrees. A connector 24 is provided on a right side surface of the main body 18. A connector of the ultrasound probe is attachably and detachably connected to the connector 24. The ultrasound probe transmits an ultrasound wave to a living body and receives a reflected wave from the living body.

The main body 18 has a case. A plurality of electronic circuits are provided in the case. The plurality of electronic circuits include a reception circuit, a transmission circuit, and a processor. The processor functions as a generator that generates an ultrasound image based on a reception signal acquired by transmitting and receiving an ultrasound wave. The display 20 is composed of a liquid crystal display (LCD), an organic LED display (OLED), and the like.

During ultrasound examination, the ultrasound image is displayed on the display 20 in an open state.

Figure 2:
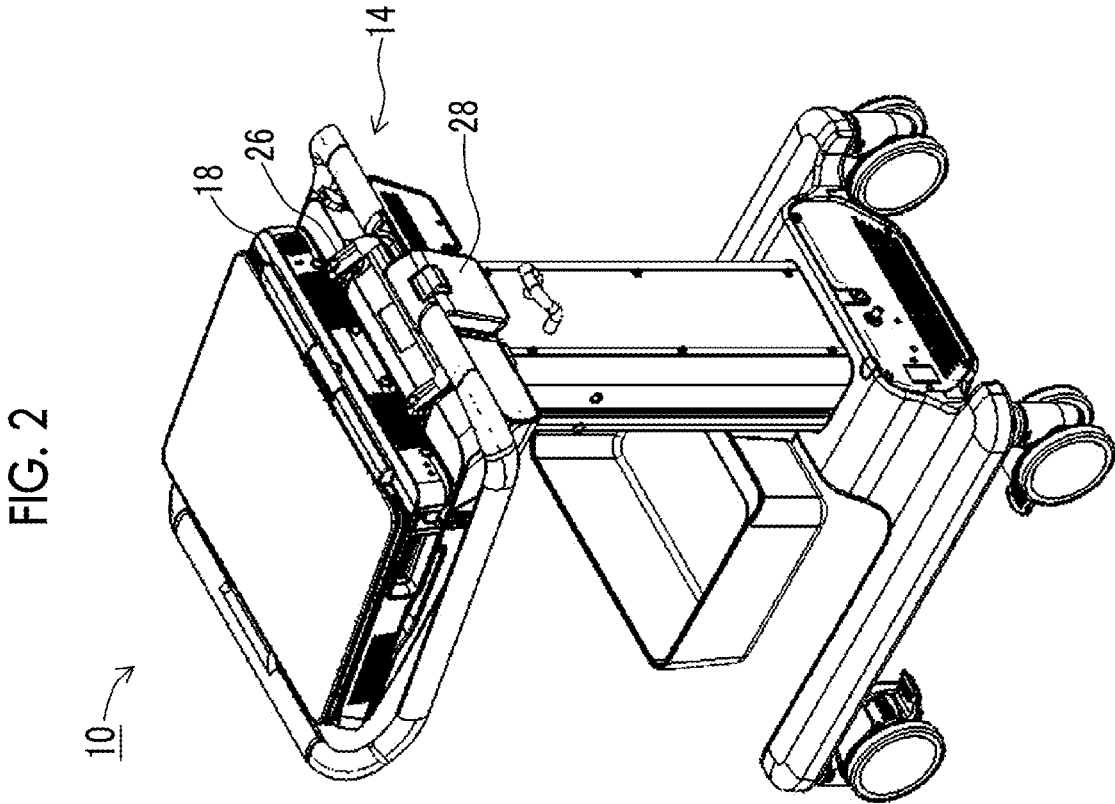
FIG. 2 is a second perspective view showing the ultrasound diagnostic apparatus according to the embodiment.

FIG. 2 shows a rear portion of the ultrasound diagnostic apparatus 10. A handle 26 is attached to a rear portion of the main body 18 to be rotatably movable. Before the main body 18 is used, the main body 18 is fixed to the cart 14, and the handle 26 is also fixed to the cart 14. In order to fix the handle 26 to the cart 14, a hook member 28 which is a movable member is provided at a rear portion of the cart 14.

Figure 3:
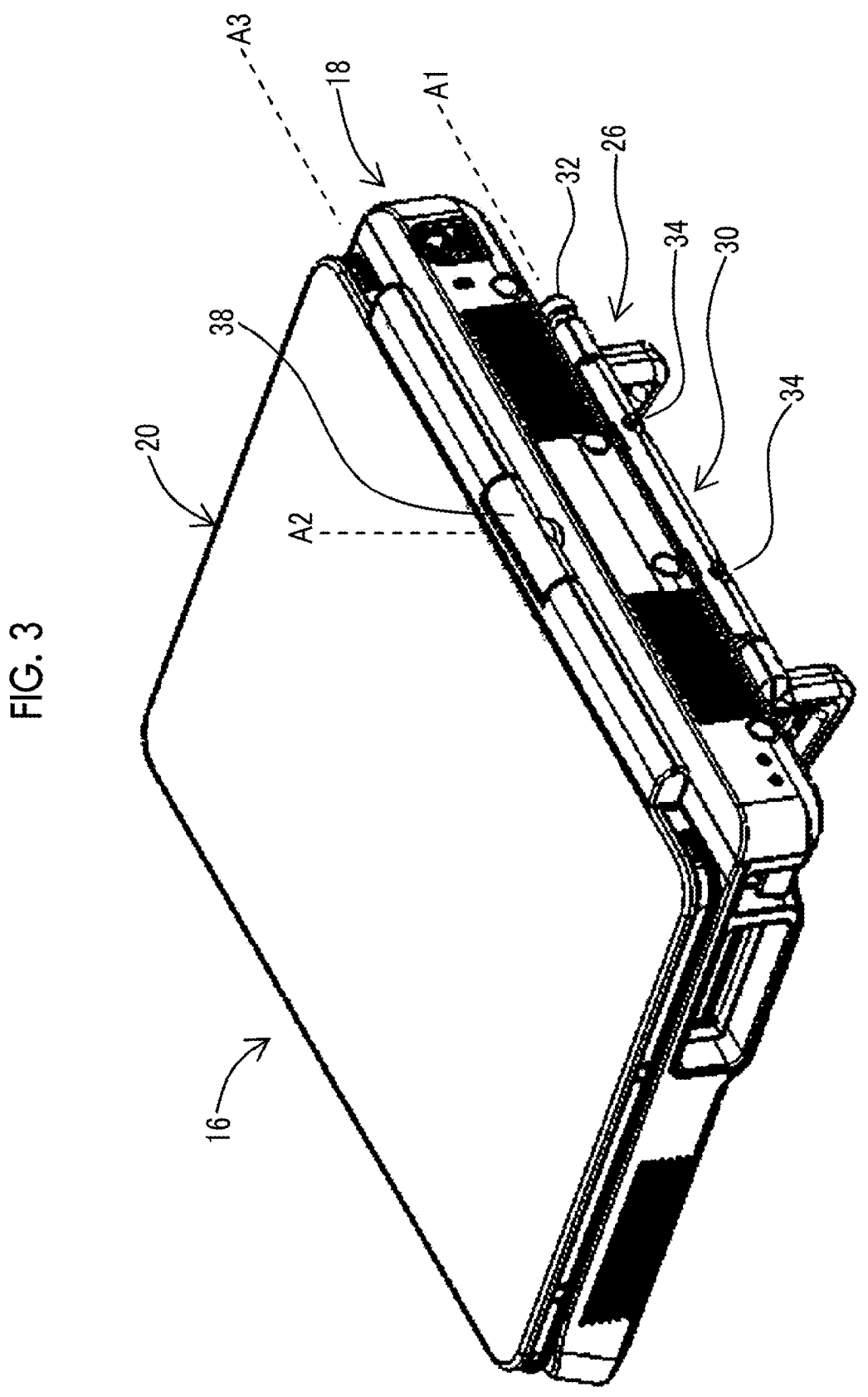
FIG. 3 is a first perspective view showing a main body unit according to the embodiment.

FIG. 3 shows a rear portion of the main body unit 16. A1 indicates a horizontal rotation axis of the handle 26. During transport of the main body unit 16, the handle 26 is locked at a first rotation angle. As shown in FIG. 3, in a case where the handle 26 is used as a stand, the handle 26 is locked at a second rotation angle.

A hinge mechanism 30 is provided on a lower surface of the rear portion of the main body 18. The hinge mechanism 30 has a hinge, a handle locking mechanism, a knob 32, and the like. The hinge has a bearing. The handle locking mechanism is a mechanism that locks a rotation angle of the handle. The knob 32 is a member that is operated in a case of unlocking the handle. The hinge mechanism 30 has two openings separated apart from each other in the right-left direction and specifically, has two pin holes 34. In a case where the main body unit 16 is fixed onto the cart, two pins are inserted into the two pin holes 34. In this case, the two pin holes 34 function as the first engaging part, and the two pins function as the second engaging part. The handle 26 is connected to the main body 18 via the hinge mechanism 30.

A support mechanism 38 is provided between the main body 18 and the display 20. The support mechanism 38 has a function of rotating the display 20 about a vertical rotation axis A2 and a function of rotating the display 20 about a horizontal rotation axis A3. The horizontal rotation axis A3 is provided above the vertical rotation axis A2.

Figure 4:
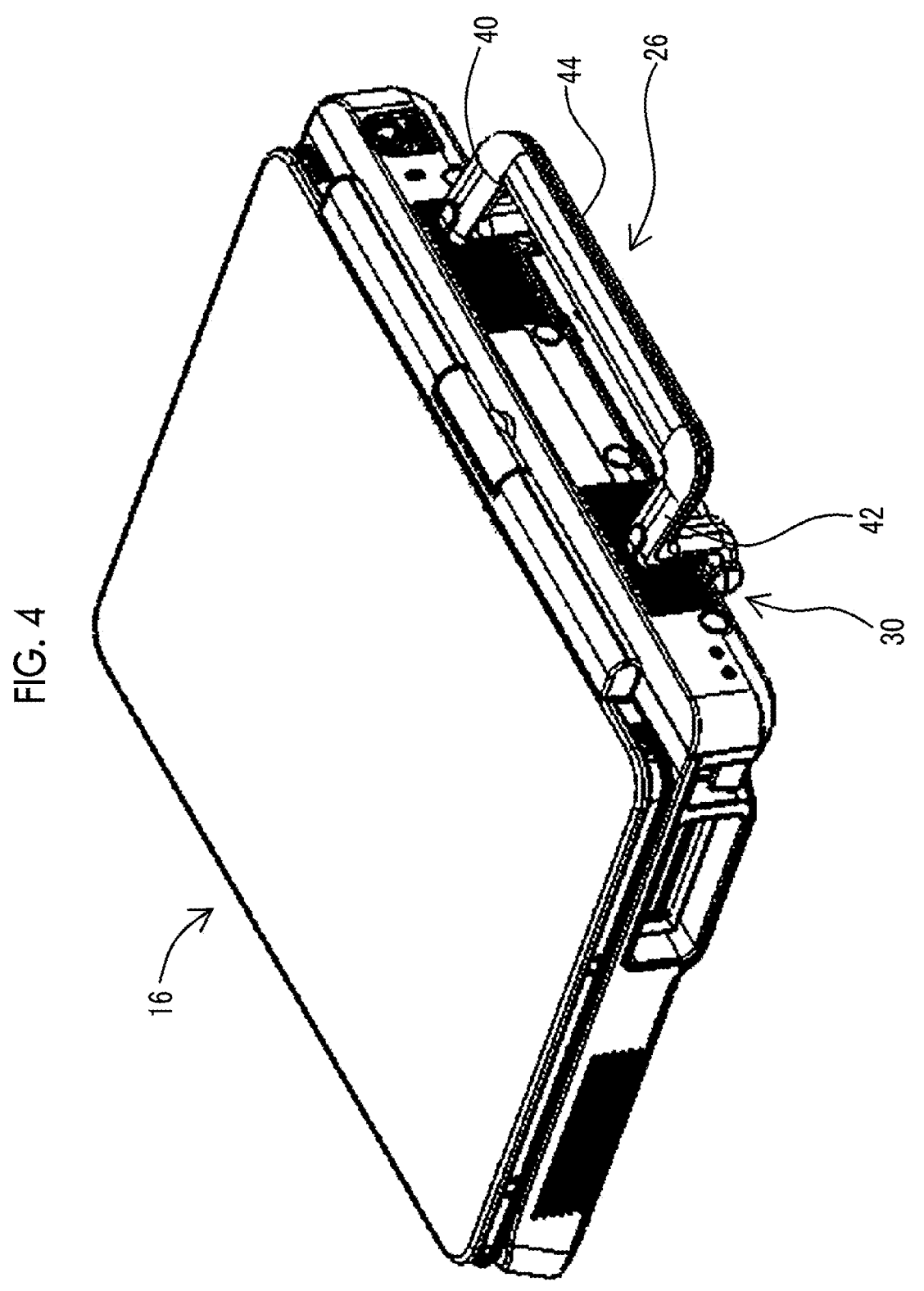
FIG. 4 is a second perspective view showing the main body unit according to the embodiment.

FIG. 4 also shows the rear portion of the main body unit 16. The handle 26 is locked at the first rotation angle. In this state, the main body unit 16 can be suspended using the handle 26, and the main body unit 16 can be transported. The handle 26 consists of a first arm 40 and a second arm 42 that are connected to the hinge mechanism 30 and a grip 44 that is connected to the first arm 40 and the second arm 42. The grip 44 is a rod-like portion gripped by a hand of the user. Each of the arms 40 and 42 has a bent form.

Figure 5:
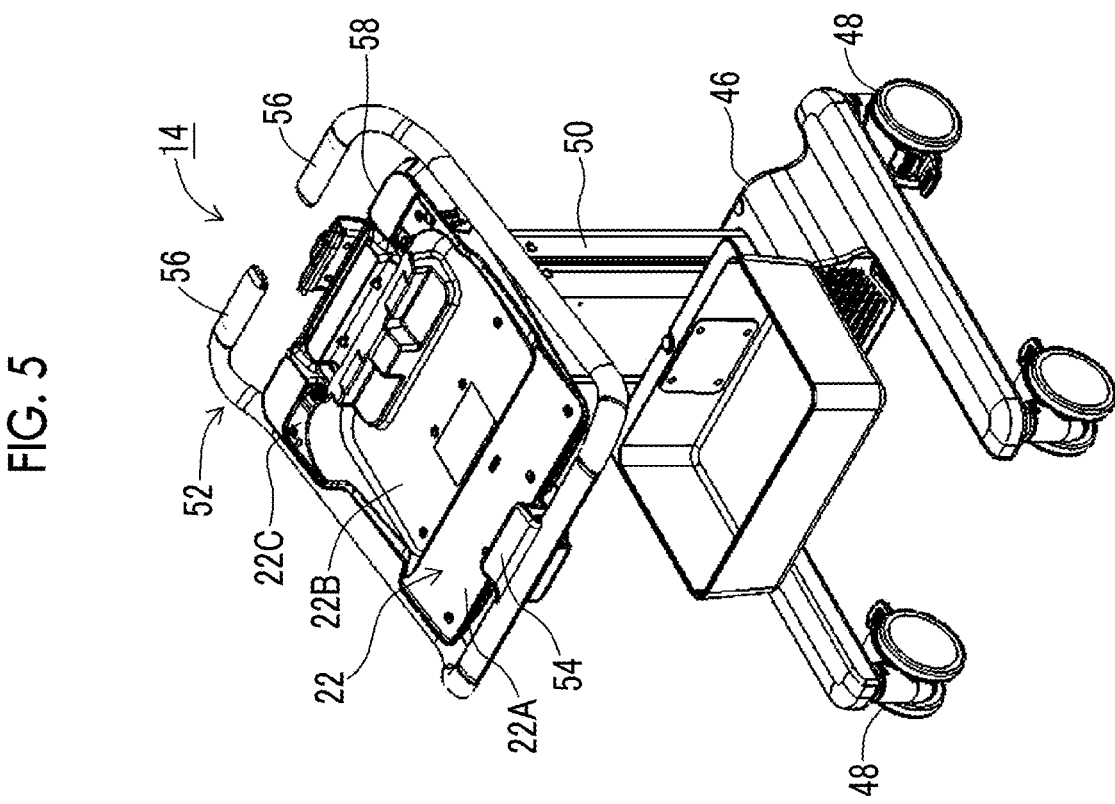
FIG. 5 is a perspective view showing a cart according to the embodiment.

FIG. 5 shows the cart 14. The cart 14 has a base 46, and four casters 48 are provided at the base 46. The base 46 supports a support column 50. The support column 50 has an expanding and contracting function. The support column 50 supports the table 22.

The table 22 consists of a front portion 22A, an intermediate portion 22B, and a rear portion 22C. The intermediate portion 22B is dented. The main body unit is placed on the front portion 22A and the rear portion 22C. The rear portion 22C is integrated with a housing 58 which is a structure. A cart handle 52 is provided to surround the table 22. The cart handle 52 has two cart grips 56. The cart handle 52 is fixed to the table 22 by a plurality of connecting members. One of the plurality of connecting members is a front block 54.

Figure 6:
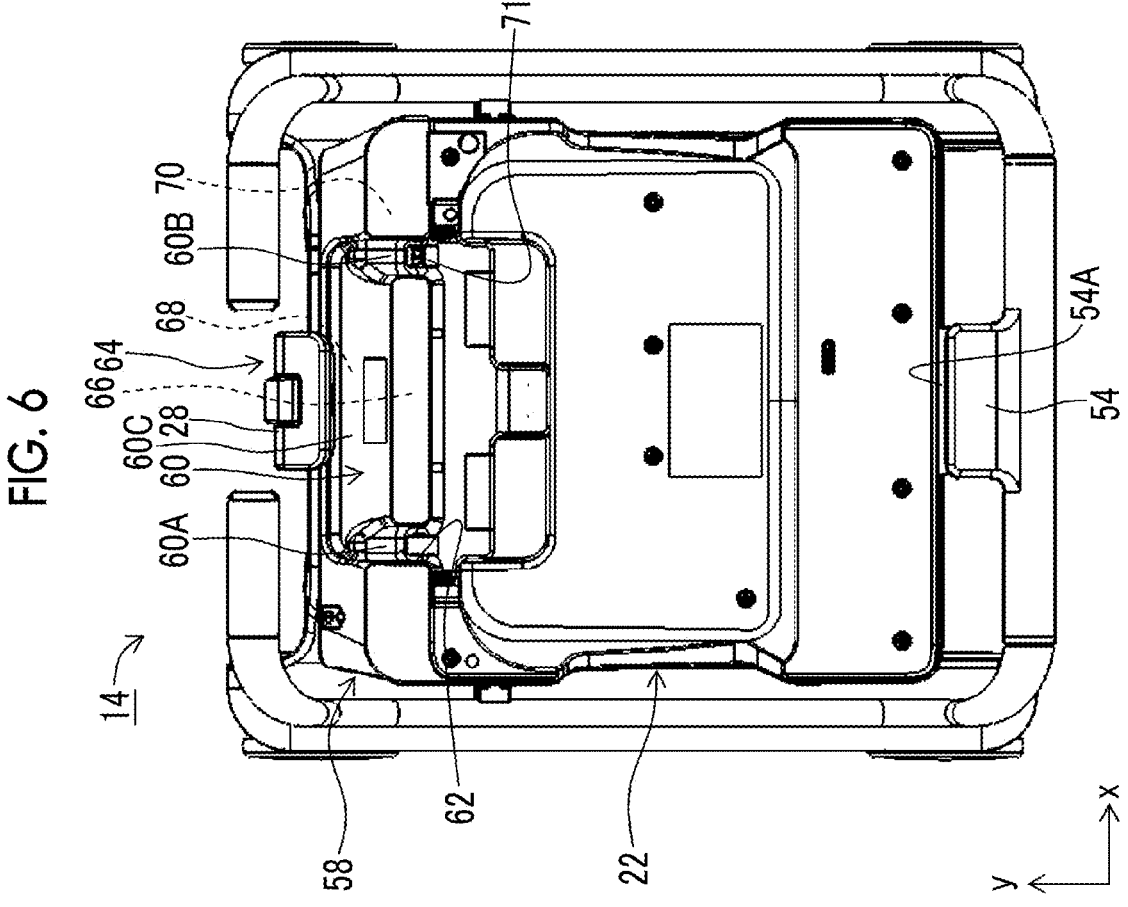
FIG. 6 is a plan view showing the cart according to the embodiment.

FIG. 6 shows an upper surface of the cart 14. The front block 54 is provided at a front portion of the table 22. A rear surface 54A of the front block 54 is a holding surface. A front portion of the main body touches the rear surface 54A, and in this state, the front portion of the main body is held by the front block 54.

The housing 58 provided at the rear portion of the cart 14 has a dented structure 60. The dented structure 60 has a first groove 60A, a second groove 60B, and a dent 60C. The dent 60C has a tray-like form. The dent 60C is continuous with the first groove 60A and the second groove 60B. The housing 58 has a contact portion that comes into contact with the knob, and the contact portion has an inclined surface 62 that pushes the knob.

The cart 14 includes a handle fixing mechanism 64, a main body fixing mechanism 66, a link mechanism 68, and a safety mechanism 70. All of these mechanisms are provided at the rear portion of the cart 14. The handle fixing mechanism 64 is provided outside the housing 58. The handle fixing mechanism 64 has the hook member 28. The main body fixing mechanism 66 and the safety mechanism 70 are accommodated in the housing 58 except for some components. The link mechanism 68 is provided across an inside and an outside of the housing 58. The link mechanism 68 may be provided outside or inside the housing 58. The safety mechanism 70 has a button 71 which is a movable member. The housing 58 has an opening, and the button 71 moves up and down through the opening.

(2-2) Main Body Fixing and Handle Fixing

Hereinafter, a process of installing the main body unit on the cart will be described, and each mechanism provided at the cart will be described.

Figure 7:
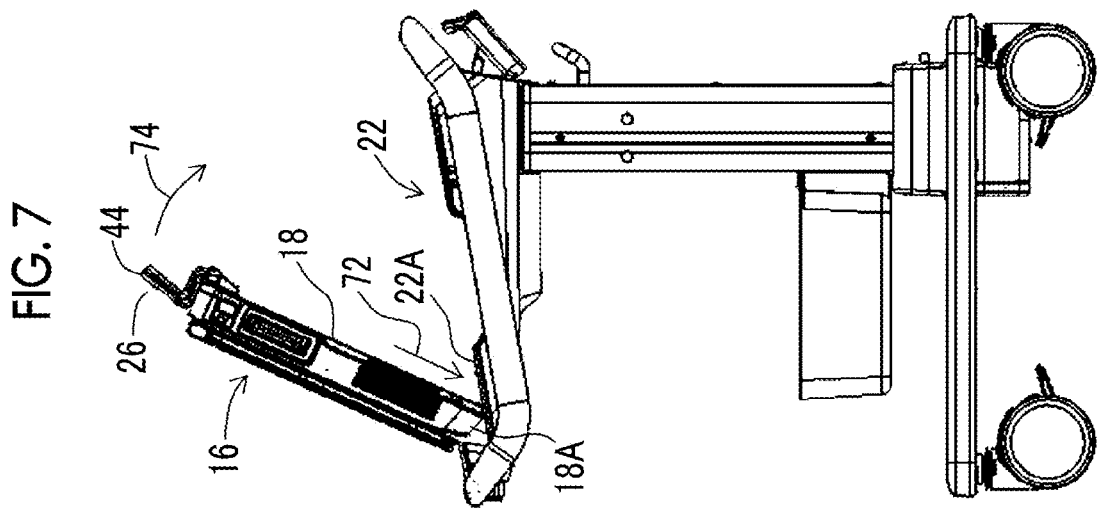
FIG. 7 is a view showing an initial state in a main body installation process.

FIG. 7 shows an initial state. The rotation angle of the handle 26 with respect to the main body 18 is the first rotation angle. The first rotation angle is 0 degrees. The handle 26 is in a locked state. The grip 44 is gripped by the user, and the main body unit 16 is suspended. In such a state, a front portion 18A of the main body 18 is placed on the front portion 22A of the table 22 (see reference numeral 72). After then, the main body unit 16 is tilted. Accordingly, the main body unit 16 is moved downward (rotatably moved) (see reference numeral 74).

Figure 8:
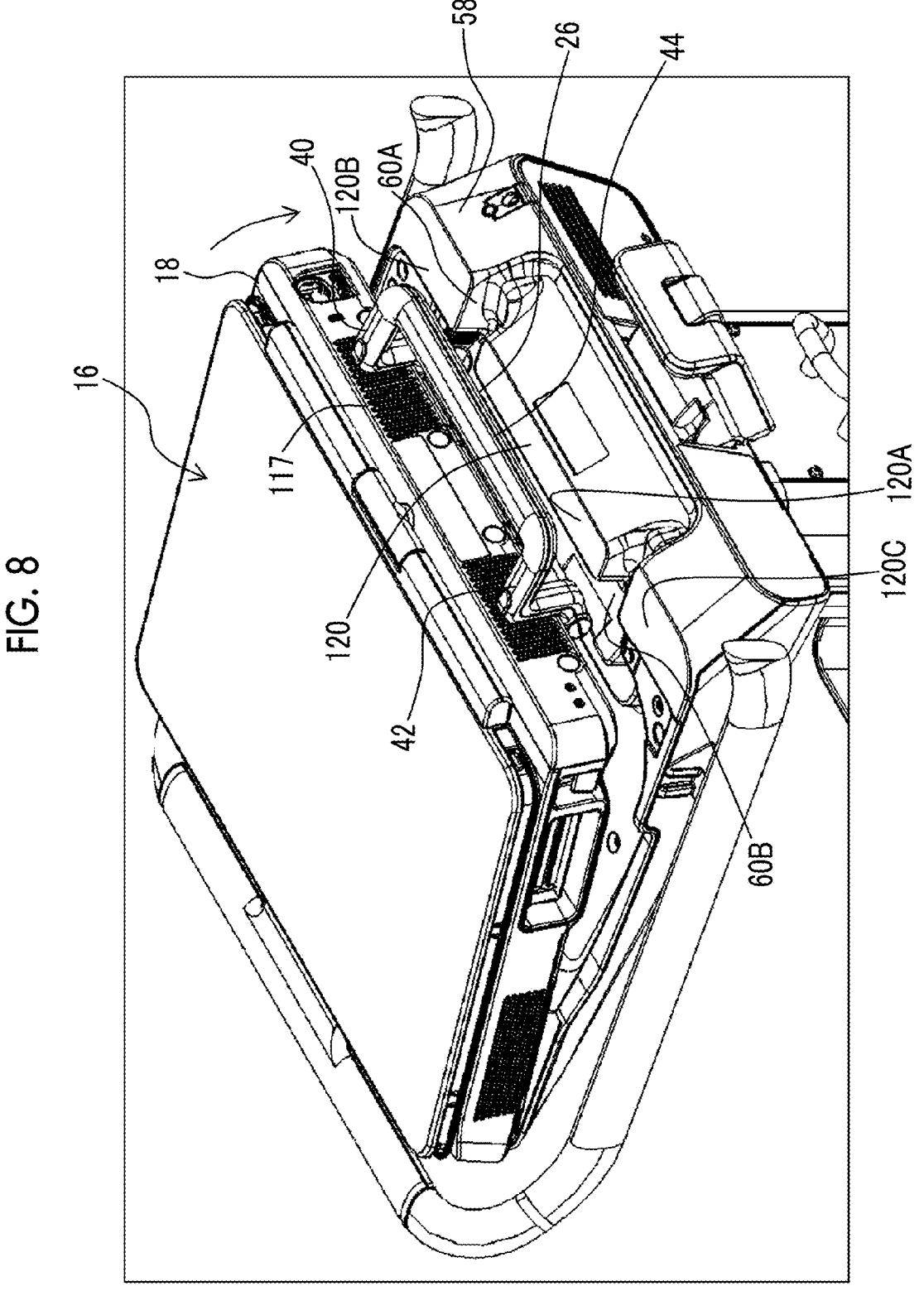
FIG. 8 is a view showing an intermediate state in the main body installation process.

FIG. 8 shows an intermediate state. The main body unit 16 has an inclined posture. The handle 26 remains locked at the first rotation angle. The handle 26 has the grip 44, the first arm 40, and the second arm 42. As the main body unit 16 moves downward, the first arm 40 is inserted into the first groove 60A, and at the same time, the second arm 42 is inserted into the second groove 60B. An exhaust port 117 is provided in a rear surface of the main body 18. The exhaust port 117 is composed of a plurality of portions arranged in the right-left direction. Exhaust air (hot air or hot wind) discharged from the exhaust port 117 flows to a rear side of the main body 18.

The housing 58 has a flat surface 120. The flat surface 120 spreads in the right-left direction and the front-rear direction and functions as an exhaust guide. As will be described later, a rear space on the rear side of the main body 18 with the exhaust port 117 as reference is defined. The flat surface 120 is near a lower surface of the rear space and spreads along the lower surface. The flat surface 120 consists of an intermediate portion 120A provided between the first groove 60A and the second groove 60B, a first end part 120B provided outside the first groove 60A in the right-left direction, and a second end part 120C provided outside the second groove 60B in the right-left direction. The right-left direction is a direction in which the first groove 60A and the second groove 60B are arranged.

Figure 9:
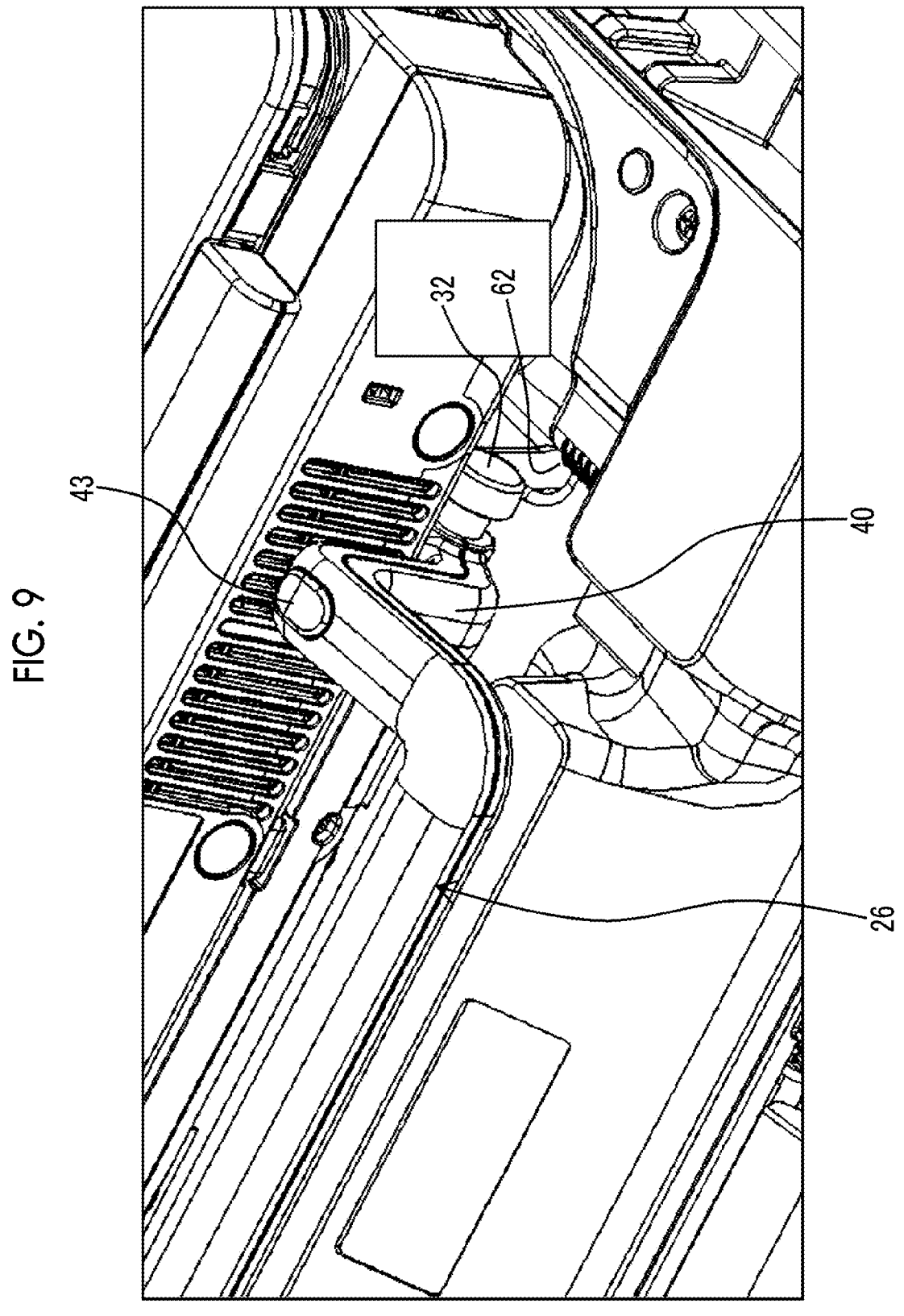
FIG. 9 is a perspective view showing a knob and an inclined surface.

FIG. 9 shows an intermediate state viewed from another angle. The hinge mechanism provided at the main body has the knob 32. The housing has the inclined surface 62 that comes into contact with the knob. The first arm 40 of the handle 26 has a bent portion, and a pad 43 is provided at the bent portion. The second arm also has a bent portion, and a pad is also provided at the bent portion. Each pad is composed of a member having a non-slip function. The handle 26 is a rigid solid member. Each pad is formed of a material softer than the handle 26.

Figure 10:
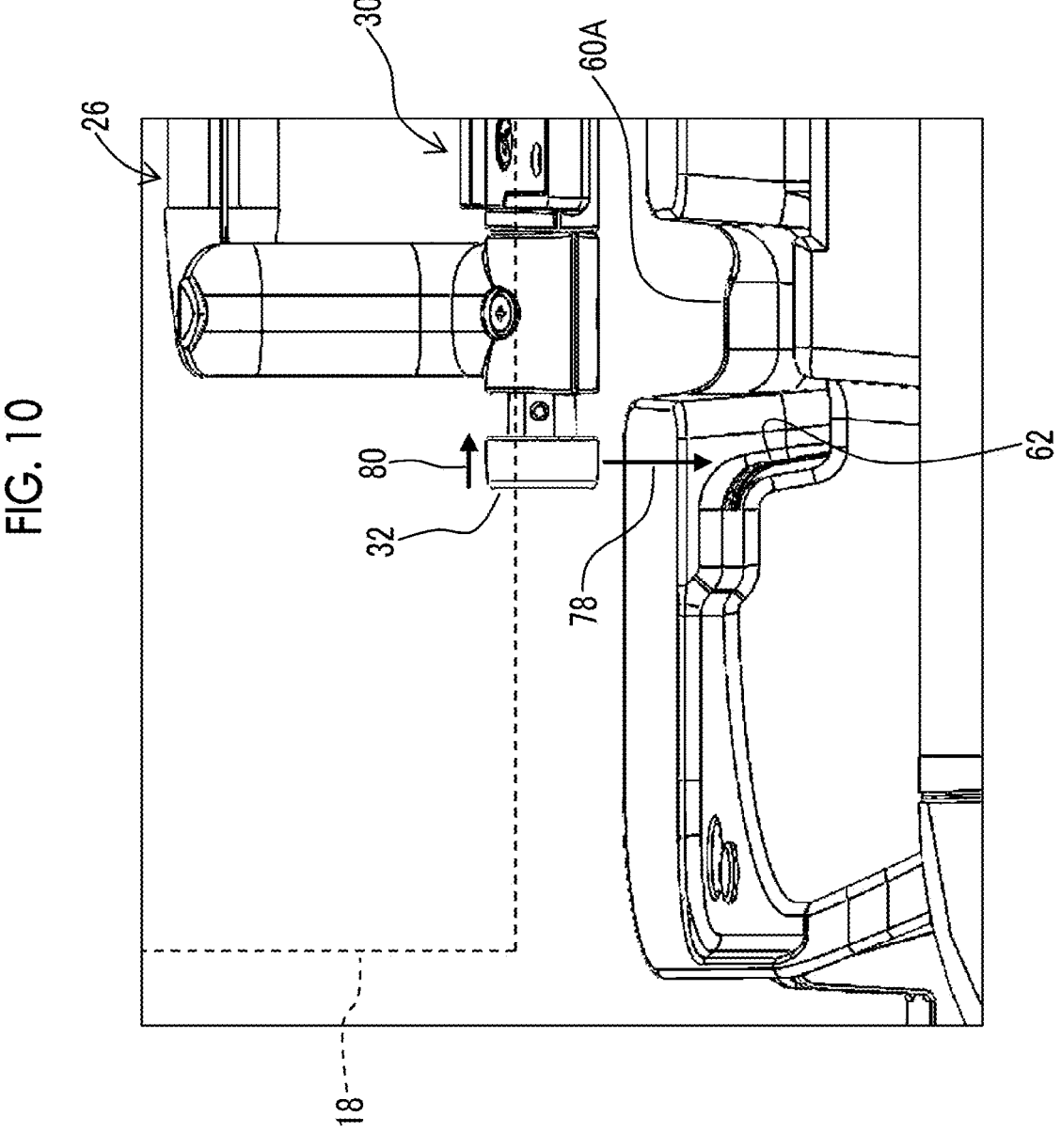
FIG. 10 is a front view showing the knob and the inclined surface.

FIG. 10 shows an intermediate state viewed from still another angle. FIG. 10 corresponds to a front view. In FIG. 10, the main body 18 is represented by a broken line. The handle 26 is connected to the hinge mechanism 30. The hinge mechanism 30 has the knob 32. The inclined surface 62 is provided in front of the first groove 60A. In a process of downward movement of the main body unit being installed on the cart, the knob 32 abuts against the inclined surface 62, and a pushing force is applied to the knob 32 from the inclined surface 62. Accordingly, the knob 32 is pushed to a handle 26 side.

Figure 11:
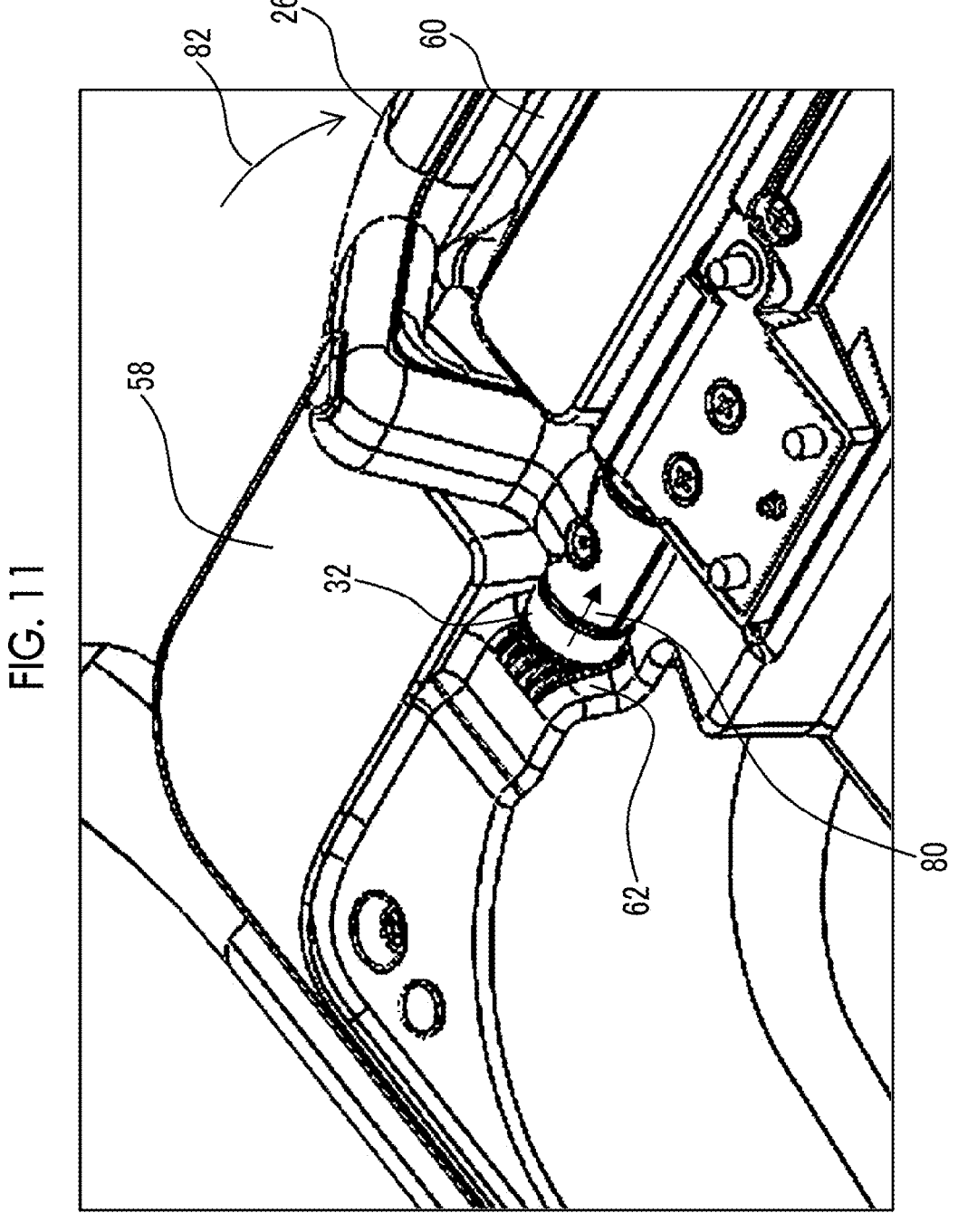
FIG. 11 is a view showing the pushed knob.

FIG. 11 shows a state where the knob 32 is pushed by the inclined surface 62 (see reference numeral 80). By pushing the knob 32, the handle is automatically unlocked, and free rotation of the handle 26 is allowed. In this state, the handle 26 is pushed and tilted to an inside by the user (see reference numeral 82), and a part of the handle 26 enters the dented structure 60 formed in the housing 58.

Figure 12:
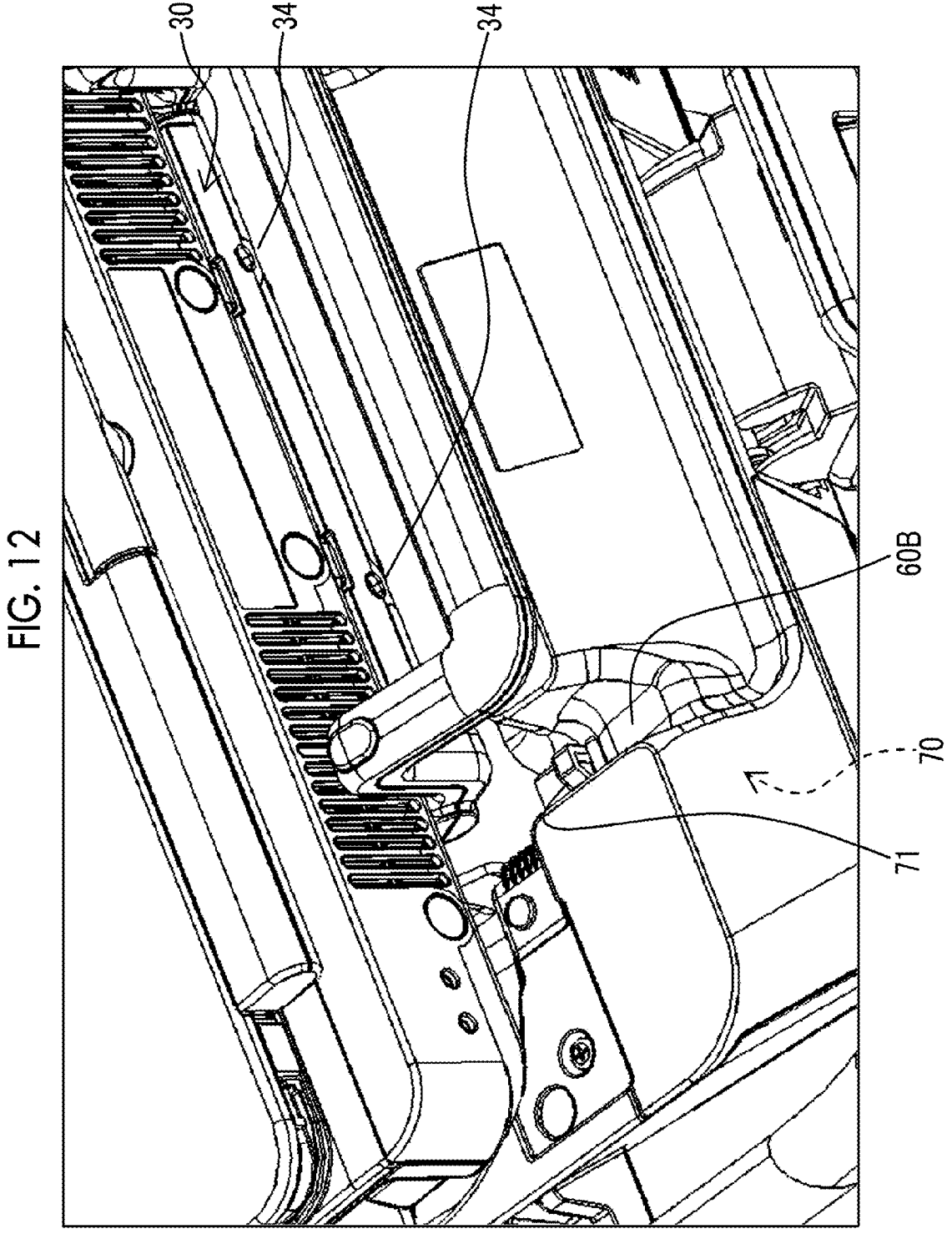
FIG. 12 is a perspective view showing a button.

FIG. 12 shows the second groove 60B in an intermediate state. The safety mechanism 70 has the button 71. The button 71 is moved up and down through an opening formed in a bottom surface (front side of the second groove 60B) of the housing. Specifically, the button 71 moves up and down between the first height and the second height. The hinge mechanism 30 has the two pin holes 34 that function as the first engaging part.

Figure 13:
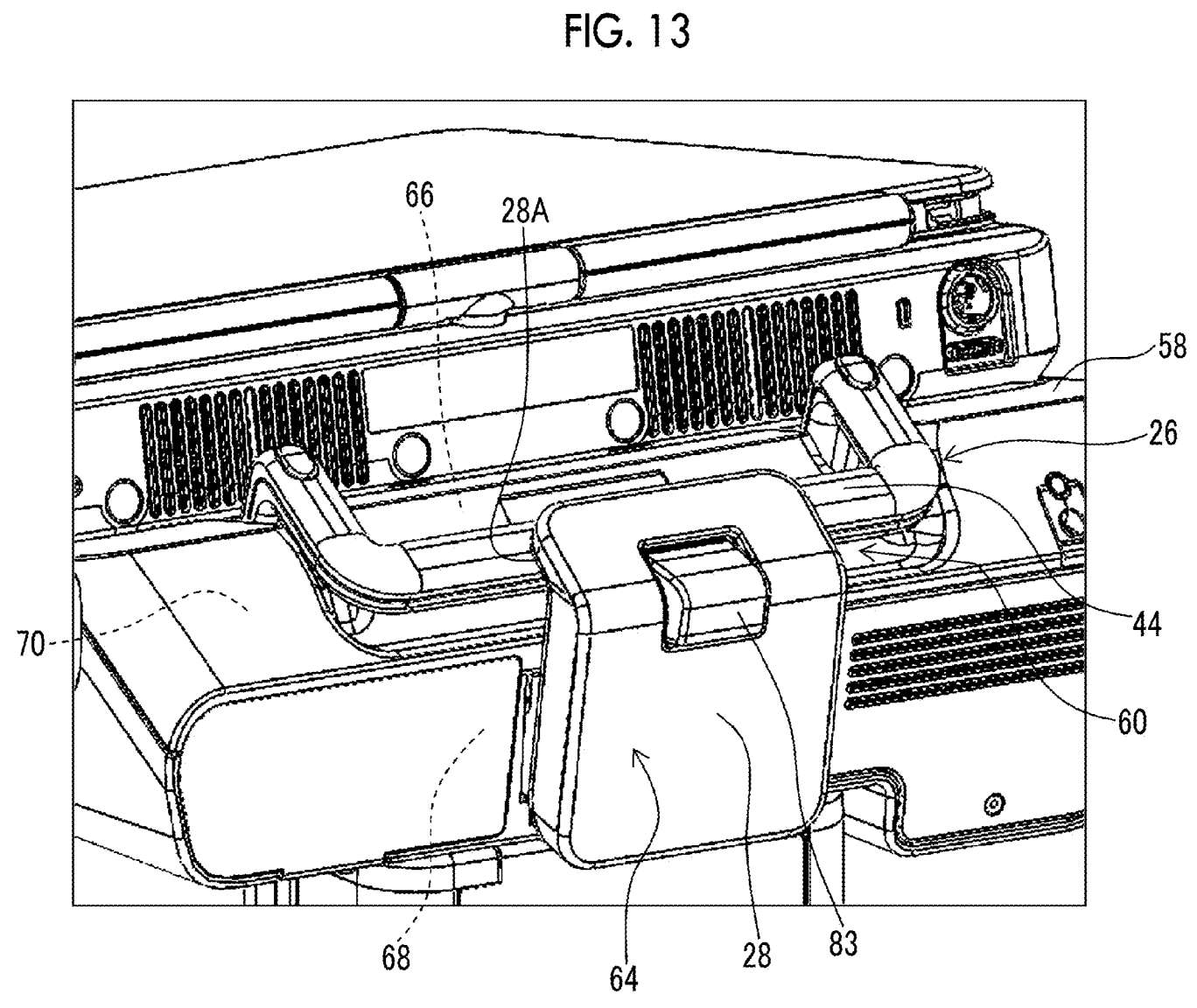

FIG. 13 shows a completed state. The rotation angle of the handle 26 is an angle for fixing the handle, and the angle is larger than the first rotation angle and smaller than the second rotation angle. The handle locking mechanism in the hinge mechanism is not operated and is in an unlocked state. However, the two arms abut against bottom surfaces of the two grooves and restrict further downward movement of the handle 26. A part of the grip 44 contactlessly enters the dented structure 60.

In FIG. 13, the handle fixing mechanism 64 is in an operation state. Specifically, the hook member 28 in the handle fixing mechanism 64 has an elevated posture, and an end part (hook) 28A of the hook member 28 is hooked on an upper surface of the grip 44. Accordingly, the handle 26 is restrained, that is, the handle 26 is fixed to the cart. In an operation state of the hook member 28, a hook locking mechanism (not shown) provided inside the hook member 28 functions, and the rotation angle of the hook member 28 is locked, that is, a hook locked state occurs. The hook locked state is released as the user operates a release button 83.

The main body fixing mechanism 66 operates via the link mechanism 68 as the handle fixing mechanism 64 operates. The safety mechanism 70 operates before the operation of the main body fixing mechanism 66. This will be described in detail below.

Figure 14:
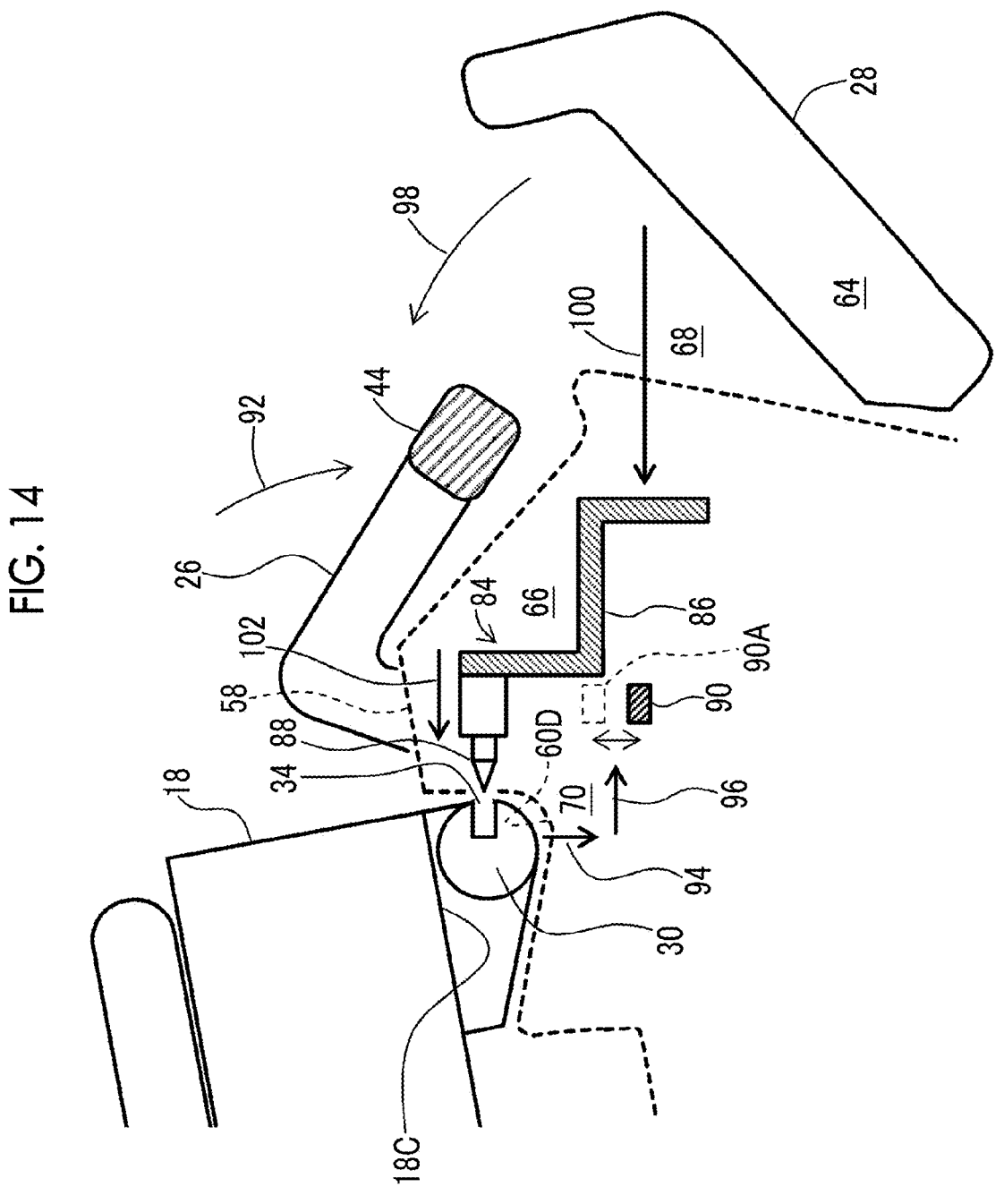
FIG. 14 is a schematic view showing a plurality of mechanisms provided in the cart.

FIG. 14 schematically shows a plurality of mechanisms provided in the cart. The handle 26 rotates to a rotation angle for fixing the handle (see reference numeral 92). The housing 58 has a lateral groove 60D that accommodates the hinge mechanism 30. An opening is formed in a bottom surface of the lateral groove 60D, and the button moves up and down through the opening. The handle fixing mechanism 64 is provided outside the housing 58, and the handle fixing mechanism 64 has the hook member 28. The hook member 28 moves rotatably about a specific rotation axis.

The main body fixing mechanism 66 and the safety mechanism 70 are provided in the housing 58. The link mechanism 68 is provided between the handle fixing mechanism 64 and the main body fixing mechanism 66. The safety mechanism 70 has a button that is pushed by a lower surface of the hinge mechanism and a stopper 90 that is retracted by downward movement of the button (see reference numerals 94 and 96).

In a case where the stopper 90 is in an operation state (see reference numeral 90A), an operation of the main body fixing mechanism 66 is prohibited. Specifically, in a case where the button is in a floated state, that is, a case where the button is positioned at the first height, without the main body unit being installed on the cart, the stopper 90 is in the operation state (see reference sign 90A). On the other hand, in a case the button is in a depressed state, that is, a case where the button is positioned at the second height, with the main body unit being installed on the cart, the stopper 90 is in a non-operation state.

The main body fixing mechanism 66 has a slider 84. The slider 84 has a frame 86 that slides. Two pins 88 which are two protrusions are fixed to the frame 86. The two pins 88 correspond to the second movable member and correspond to the second engaging part.

The hinge mechanism 30 is provided at a lower surface 18C of the rear portion of the main body 18. The hinge mechanism 30 has the two pin holes 34 which are two openings. The two pin holes 34 correspond to the first engaging part. In a case where the two pins 88 are inserted into the two pin holes 34, that is, in a case where the second engaging part is engaged with the first engaging part, the main body 18 is fixed to the cart. The main body cannot be detached from the cart unless the fixed state is released.

In summary, in FIG. 14, in a case where the main body 18 is installed on the cart, the safety mechanism 70 allows forward movement of the slider 84. In this state, the hook member 28 is rotated to hook the hook member 28 on the grip 44 (see reference numeral 98), thereby a fixed state of the handle 26 is formed. In this case, movement of the hook member 28 is transmitted to the main body fixing mechanism 66 via the link mechanism 68. Accordingly, the slider 84 moves forward (see reference numeral 102), and the two pins 88 are inserted into the two pin holes 34. Accordingly, a main body fixed state is formed.

Figure 15:
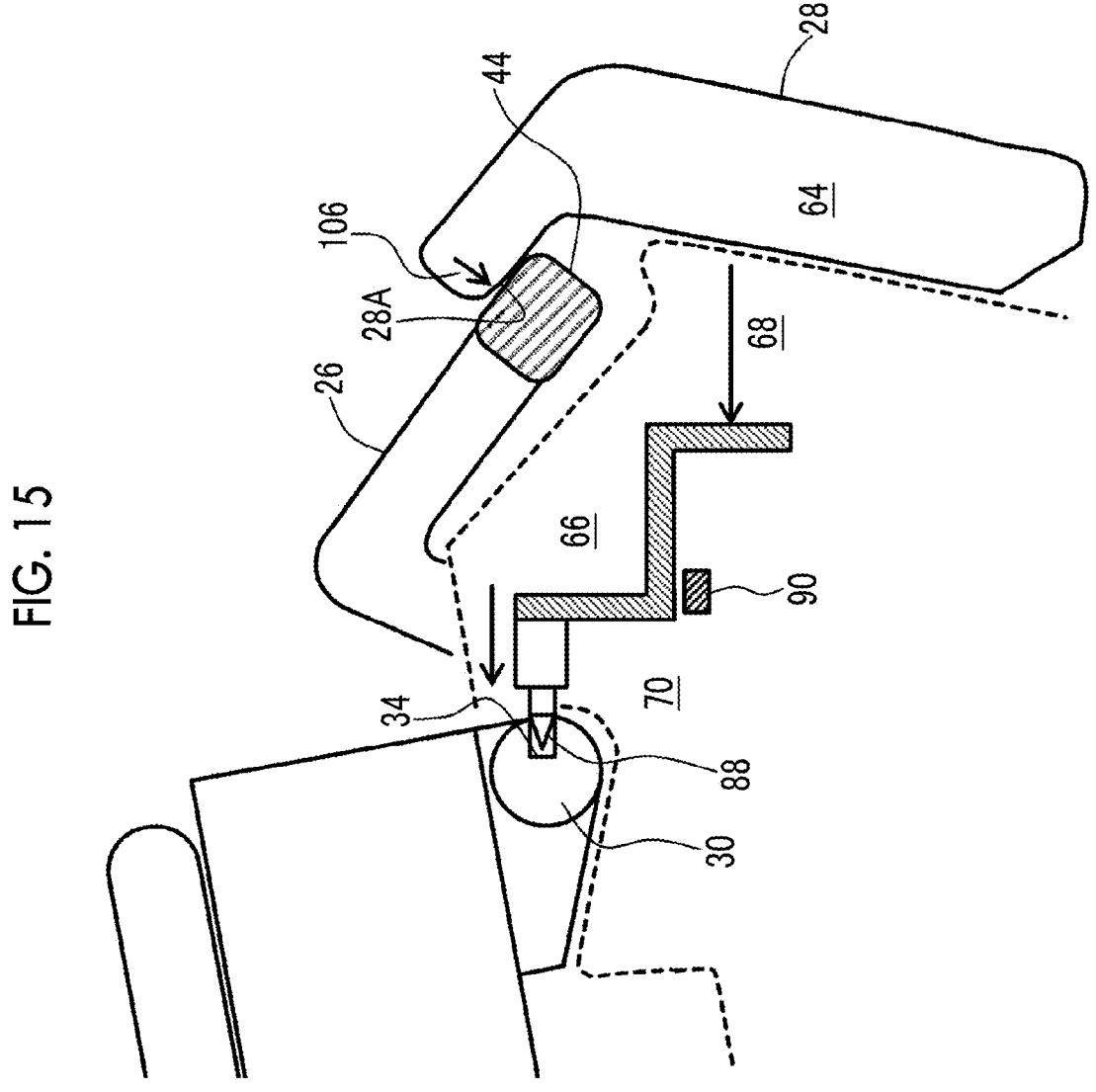
FIG. 15 is a schematic view showing a handle fixed state and a main body fixed state.

FIG. 15 shows a main body fixed state and a handle fixed state. The end part 28A of the hook member 28 in the handle fixing mechanism 64 presses the grip 44 of the handle 26, and a pushing force 106 is applied from the end part 28A to the grip 44. Due to the action of the link mechanism 68, movement of the slider in the main body fixing mechanism 66 occurs from the movement of the hook member 28. The stopper 90 in the safety mechanism 70 is in a retracted state. The two pins 88 of the main body fixing mechanism 66 are inserted into the two pin holes 34 of the hinge mechanism 30.

Figure 16:
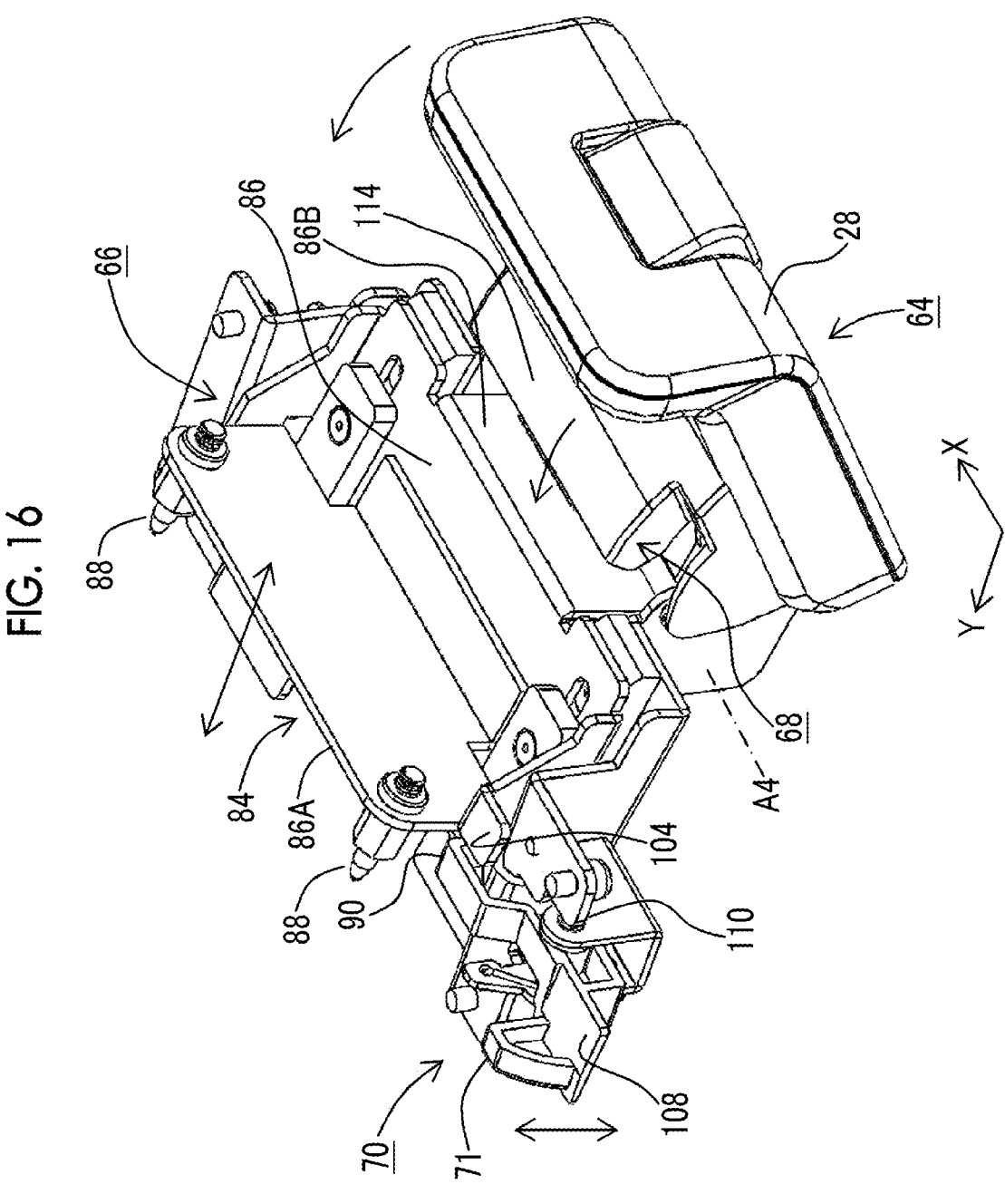
FIG. 16 is a perspective view showing an assembly in an operation restricted state.

FIG. 16 shows an assembly provided in the cart. The assembly corresponds to specific examples of the handle fixing mechanism 64, the main body fixing mechanism 66, the link mechanism 68, and the safety mechanism 70. An operation of the main body fixing mechanism 66 is restricted by the safety mechanism 70.

The handle fixing mechanism 64 has the hook member 28 that moves rotatably about a horizontal rotation axis A4. A member 114 that protrudes forward is provided on the front side of the hook member 28, and the member 114 functions as the link mechanism 68.

The main body fixing mechanism 66 has the slider 84, and the slider 84 has the frame 86. The frame 86 has a plate 86A and a plate 86B. A pushing force from the link mechanism 68 is applied to the plate 86B. The two pins 88 are fixed to the plate 86A. The frame 86 has a protrusion 104.

The safety mechanism 70 has the button 71 that moves up and down and a seat 108 comprising the button 71. The seat 108 moves rotatably (seesaw motion) around a rotation shaft 110. An end part of the seat 108 is the stopper 90. The stopper 90 is present on the front side of the protrusion 104, and the forward movement of the slider 84 is prohibited. In FIG. 16, a Y-direction is a slide direction of the slider 84. An X-direction is a horizontal direction orthogonal to the Y-direction.

Figure 17:
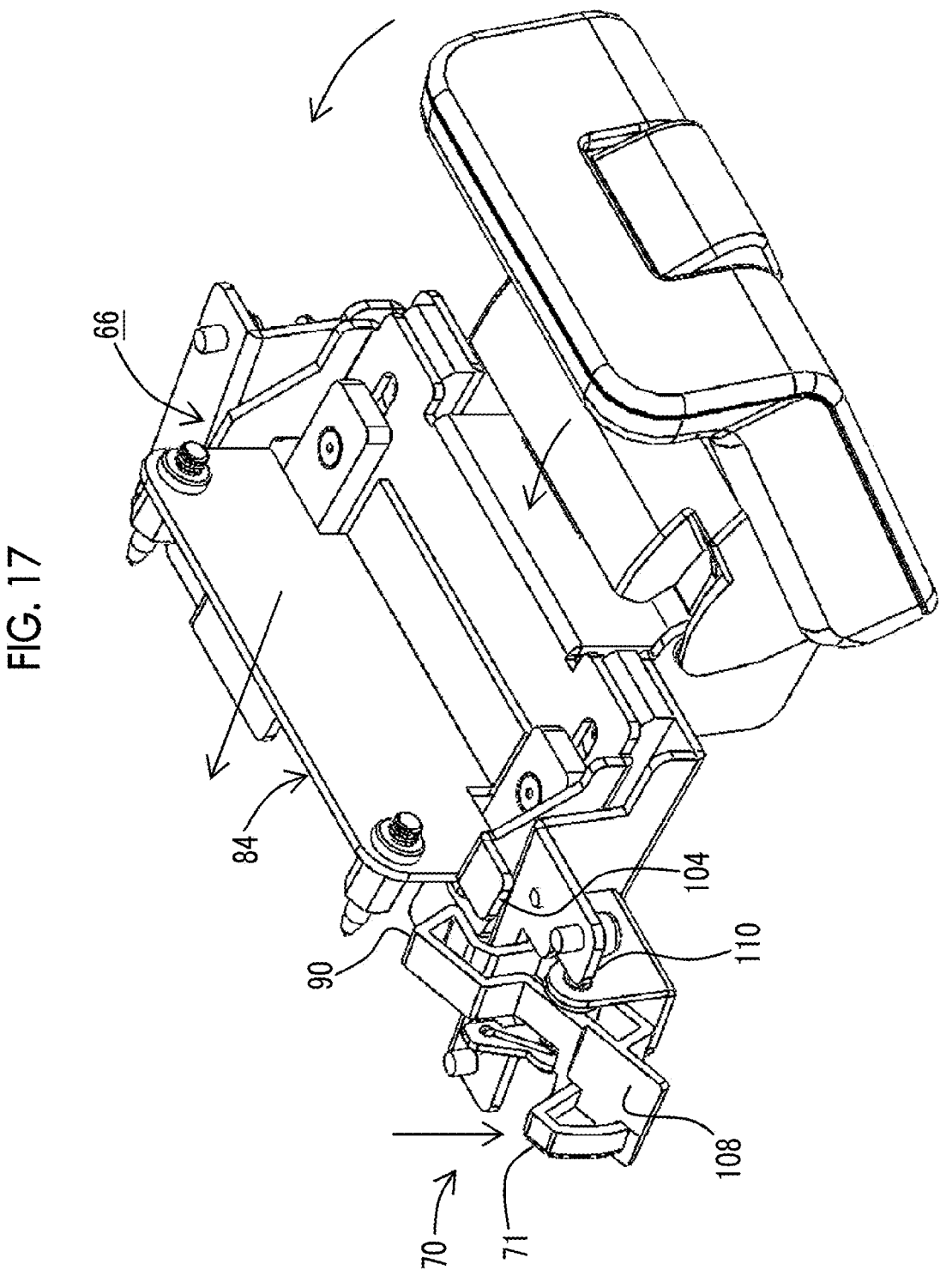
FIG. 17 is a perspective view showing the assembly in an operation restriction released state.

In FIG. 17, the safety mechanism 70 allows the main body fixing mechanism 66 to operate. Specifically, the button 71 is depressed, and the seat 108 is inclined. The stopper 90 provided on the seat 108 is retracted upward. In this state, even in a case where the protrusion 104 moves forward, the protrusion 104 does not collide with the stopper 90. That is, the forward movement of the slider 84 is allowed. A retracting force is applied to the slider 84 from a spring (not shown). Accordingly, the slider 84 naturally does not move forward.

Figure 18:
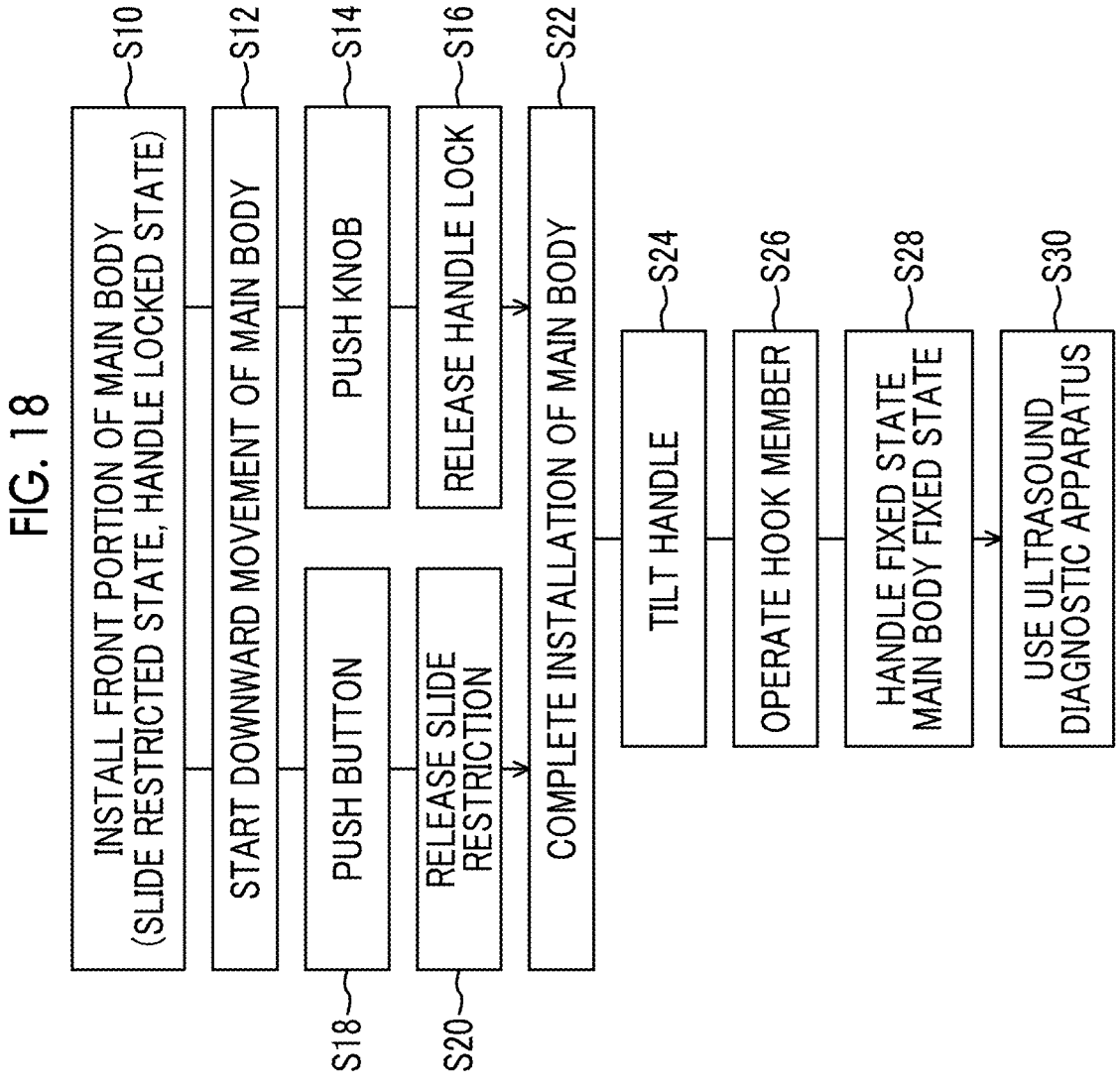
FIG. 18 is a flowchart showing the main body installation process.

FIG. 18 is a flowchart showing a main body installation process. In S10, the front portion of the main body is placed on the cart. A slide restricted state is formed by the safety mechanism, and a handle locked state is formed by the handle locking mechanism. The handle locked state is a state where the handle is locked with respect to the main body and is different from a state where the handle is fixed to the cart.

In S12, the downward movement of the main body is started. In S14, the knob is pushed by the knob touching the inclined surface. Accordingly, in S16, the handle lock state is released. On the other hand, in S18, the button is pushed by the bottom surface of the hinge mechanism. Accordingly, in S20, slide restriction is released by the safety mechanism. That is, the main body fixing mechanism can be operated.

In S22, the installation of the main body on the cart is completed. In S24, the handle is tilted to the inside by the user. In S26, the hook member is operated by the user, and a state where the hook member is hooked on the grip occurs. That is, in S28, the handle fixed state occurs. The movement of the hook member is transmitted to the main body fixing mechanism, and the main body fixing mechanism is operated. The two pins of the main body fixing mechanism are inserted into the two pin holes on a main body side. Accordingly, the main body fixed state is formed in S28. After then, in S30, ultrasound examination of a subject is performed using the ultrasound diagnostic apparatus. In S30, the main body unit may be transported using the cart.

With the above configuration, the handle is fixed to the cart in addition to the fixing of the main body to the cart, so that the fixed state of the main body can be made firmer. Since the free movement of the handle is prohibited during the use of the main body unit, problems such as collision of the handle with another member and occurrence of an overload caused by lifting of the handle do not occur.

In addition, with the above configuration, since the handle lock and the slide lock are naturally released in a process of tilting the main body unit, the user does not have a burden in response to such releases. With the safety mechanism, in a case where the main body is not installed on the cart, the operation of the main body fixing mechanism is prohibited, so that the two pins do not inadvertently protrude. Accordingly, the main body does not collide with the two pins.

Figure 19:
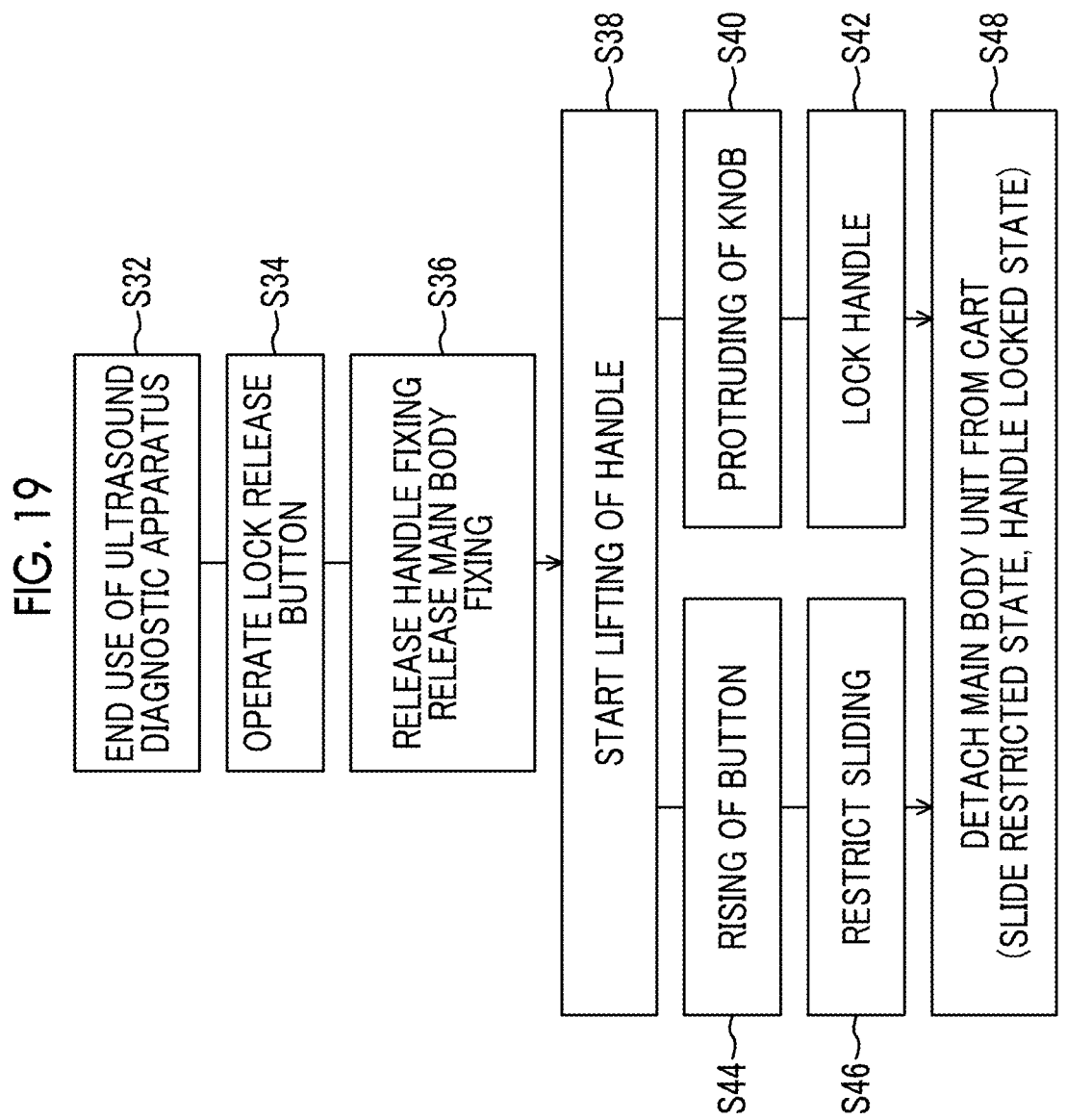
FIG. 19 is a flowchart showing a main body detachment process.

FIG. 19 is a flowchart showing a process in a case of detaching the main body from the cart. In S32, the use of the ultrasound diagnostic apparatus is ended. For other reasons, the main body unit may be detached from the cart.

In S34, the hook member is tilted rearward by an operation of a lock release button. In S36, handle fixing is released, and at the same time, main body fixing is released. In S38, the grip in the handle is gripped by the user, and the grip is pulled upward. Accordingly, the main body unit moves rotatably.

In S40, the knob protrudes due to disengagement of the knob from the inclined surface, and in S42, the handle locked state occurs. A minimum rotation angle of the handle is the first rotation angle, that is, 0 degrees, and the handle is locked at the angle. The handle lock is maintained unless the knob is operated thereafter.

On the other hand, in S44, the button floats as the main body unit is pulled, and specifically, the button rises from the second height to the first height. Accordingly, in S46, an operation of the main body fixing mechanism is prohibited, that is, sliding of the slider is prohibited. In S48, the main body unit is detached from the cart. The slide restricted state is maintained, and the handle locked state is also maintained.

(2-3) Relationship Between Rear Space and Standby Location

Figure 20:
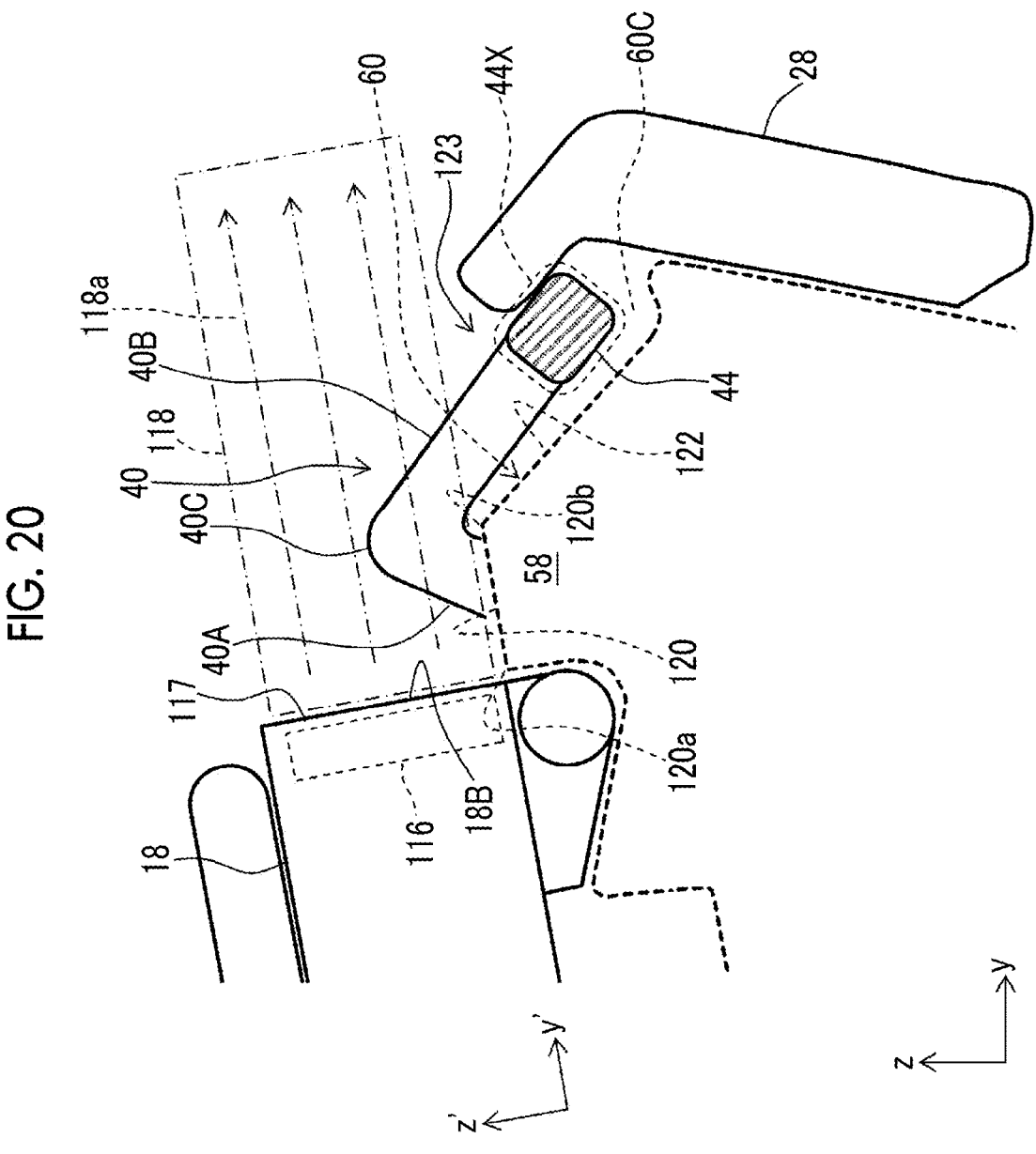
FIG. 20 is a view showing a rear space and a standby location.

FIG. 20 shows the rear portions of the main body 18 and the cart. The x-direction is the horizontal direction, which is the front-rear direction of the ultrasound diagnostic apparatus. The z-direction is a vertical direction, which is the up-down direction of the ultrasound diagnostic apparatus. The main body 18 is inclined on the cart. A y'-direction and a z'-direction are directions defined with the inclined main body 18 as reference. The y'-direction is a direction parallel to a central axis of the main body 18 and is the depth direction of the main body 18. The z'-direction is a direction orthogonal to the central axis of the main body 18, which is the height direction of the main body 18. The central axis of the main body 18 is an imaginary axis passing through a center of the front portion and a center of the rear portion of the main body 18.

The main body 18 has a rear surface 18B that faces rearward. In the example shown in the drawing, the rear surface 18B is a surface orthogonal to the central axis of the main body 18. The exhaust port 117 is provided in the rear surface 18B. The exhaust port 117 consists of a plurality of portions arranged in the right-left direction. A fan unit 116 is provided at the rear portion of the main body 18. The fan unit 116 consists of a plurality of fans arranged in the right-left direction.

A rear space 118 is defined by moving the exhaust port 117 rearward (y'-direction) in an imaginarily parallel manner. The rear space 118 is a three-dimensional space and specifically consists of a plurality of cubic spaces corresponding to a plurality of portions constituting the exhaust port 117. A space below the rear space 118 is a lower space 123.

The housing 58 supports the rear portion of the main body 18. The housing 58 has the flat surface 120 that functions as the exhaust guide. The flat surface 120 is near the lower surface of the rear space 118 and spreads two-dimensionally along the lower surface. The flat surface 120 is provided at a position close to the exhaust port 117, and a front edge 120a of the flat surface 120 is near a lower edge (a lower edge of the exhaust port 117) of the rear surface 18B. An inclined surface 122 spreads from a rear edge 120b of the flat surface 120 in an oblique downward direction. The inclined surface 122 is a bottom surface of the dent 60C in the dented structure 60. The dent 60C has a form of a tray.

The handle has the two arms. The first arm 40 has a first portion 40A connected to the hinge mechanism and a second portion 40B connected to the grip 44 and further has a bent portion 40C between the first portion 40A and the second portion 40B. The second arm also has the same configuration as that of the first arm 40.

The first portion 40A and the bent portion 40C enter a lower portion of the rear space 118. Most of the second portion 40B belongs to the lower space 123. In a case where the rear side (to be specific, the y'-direction) is viewed from the exhaust port 117, the first portion 40A and the second portion 40B overlap each other. In other words, the second portion 40B is hidden behind the first portion 40A and the bent portion 40C. The same applies to the second arm.

The cart has a standby location 44X provided below the rear space 118. The standby location 44X is a location where the grip 44 is positioned in a case of fixing the handle. The standby location 44X belongs to the lower space 123 and is near the inclined surface 122. In a case where the grip 44 is positioned at the standby location 44X, the grip 44 is not in contact with the housing 58. There is a gap between the grip 44 and the inclined surface 122 into which a fingertip can enter. The first arm and the second arm abut against the bottom surface of the first groove and the bottom surface of the second groove, and a floating force of the button acts on the second arm. Therefore, in FIG. 20, further rotation of the handle in a clockwise direction is restricted.

Exhaust air discharged from the exhaust port 117 is guided to the flat surface 120 and is generally directed rearward (see reference numeral 118a) while being diffused to some extent. It is considered that some of the exhaust air travels in the oblique downward direction along the inclined surface 122, but the amount of some of the exhaust air is small. Some of the exhaust air travels while being diffused. The amount of the exhaust air reaching the grip 44 is small. That is, the amount of heat applied to the grip 44 from the exhaust air is small. The inclined surface 122 and the grip 44 are in a contactless relationship, and direct heat conduction does not occur therebetween. Although the hook member 28 is in contact with the grip 44, the hook member 28 is a member provided at an innermost position in the cart. Thus, heat conduction from the hook member 28 to the grip 44 can be practically ignored.

In a case where the first arm 40 is focused, exhaust air discharged from the exhaust port 117 abuts against the first portion 40A and the bent portion 40C, and a temperature rise occurs in these portions. Heat conduction from the bent portion 40C to the second portion 40B can occur. However, the amount of exhaust air abutting against the second portion 40B is small, and heat radiation to the outside is expected in the second portion 40B. Accordingly, in the second portion 40B, the temperature decreases as a distance to the grip 44 decreases. In the end, the amount of heat transmitted from the second portion 40B to the grip 44 is small. The same applies to the second arm.

Accordingly, even in a case where exhaust air is released from the exhaust port, a temperature rise of the grip 44 is small. Conversely, the standby location 44X is determined such that the grip 44 does not become hot. Even in a case where the grip 44 is gripped when detaching the main body unit from the cart after ultrasound examination, the user does not feel heat or discomfort.

(2-4) Handle and Handle Lock

Figure 21:
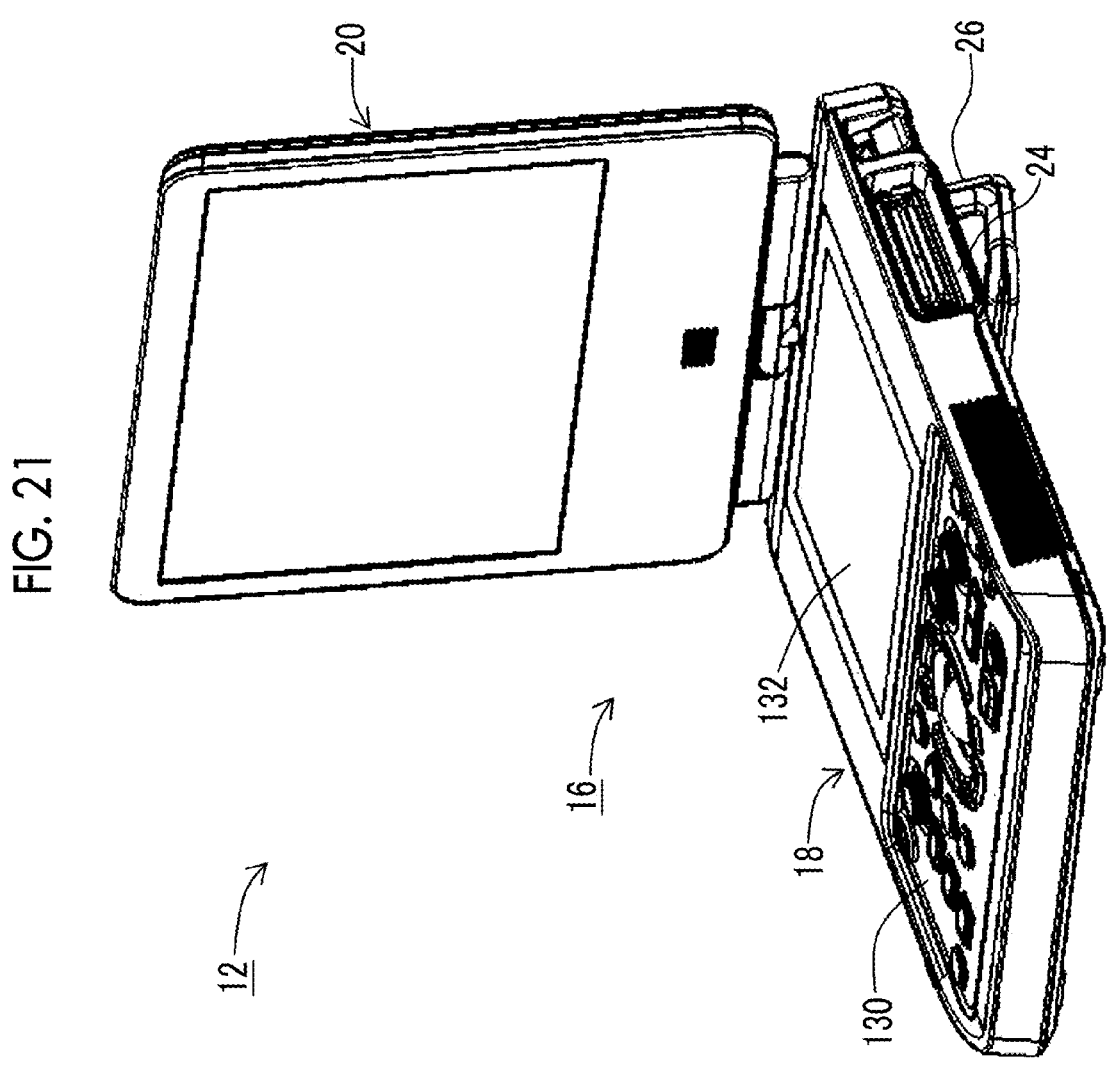
FIG. 21 is a perspective view showing a use state of the main body unit.

FIG. 21 shows the ultrasonic diagnostic device 12 placed on a general-purpose table. The ultrasound probe is not shown. The main body unit 16 is composed of the main body 18 that generates an ultrasound image and the display 20 that displays the ultrasound image. The display 20 is in an open state. The main body 18 has an operation panel 130 and a touch screen panel 132. The main body 18 has the connector 24 to which the ultrasound probe is connected.

The handle 26 is attached to the rear portion of the main body 18 to be rotatably movable. In FIG. 21, the handle 26 is locked at the second rotation angle, and the handle 26 is used as a stand.

Figure 22:
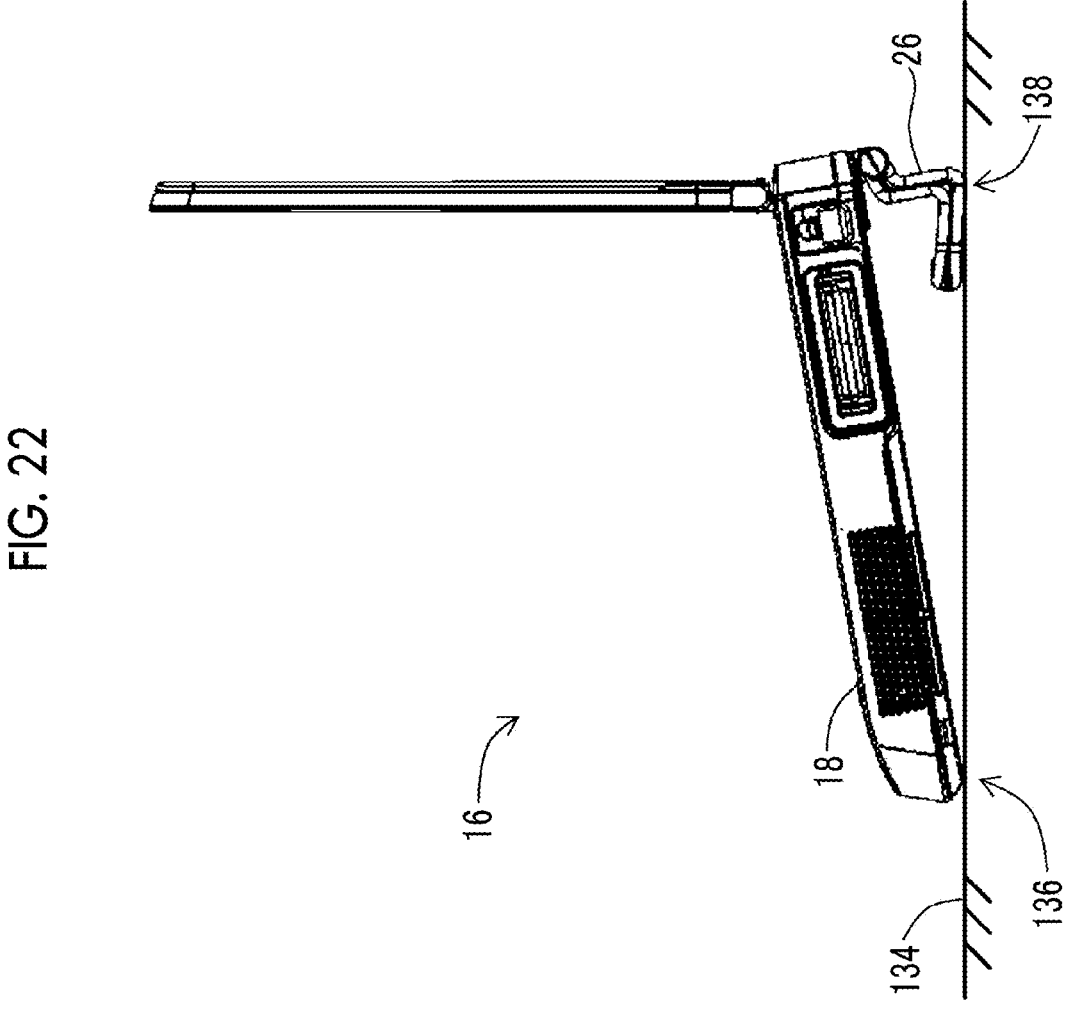
FIG. 22 is a side view showing the use state of the main body unit.

FIG. 22 shows a side surface of the main body unit 16. A table surface 134 is a flat surface, and the main body unit is placed on the table surface 134. Specifically, the front portion of the main body 18 is in contact with the table surface 134 (see reference numeral 136), and the two bent portions of the handle 26 are in contact with the table surface 134 (see reference numeral 138).

Figure 23:
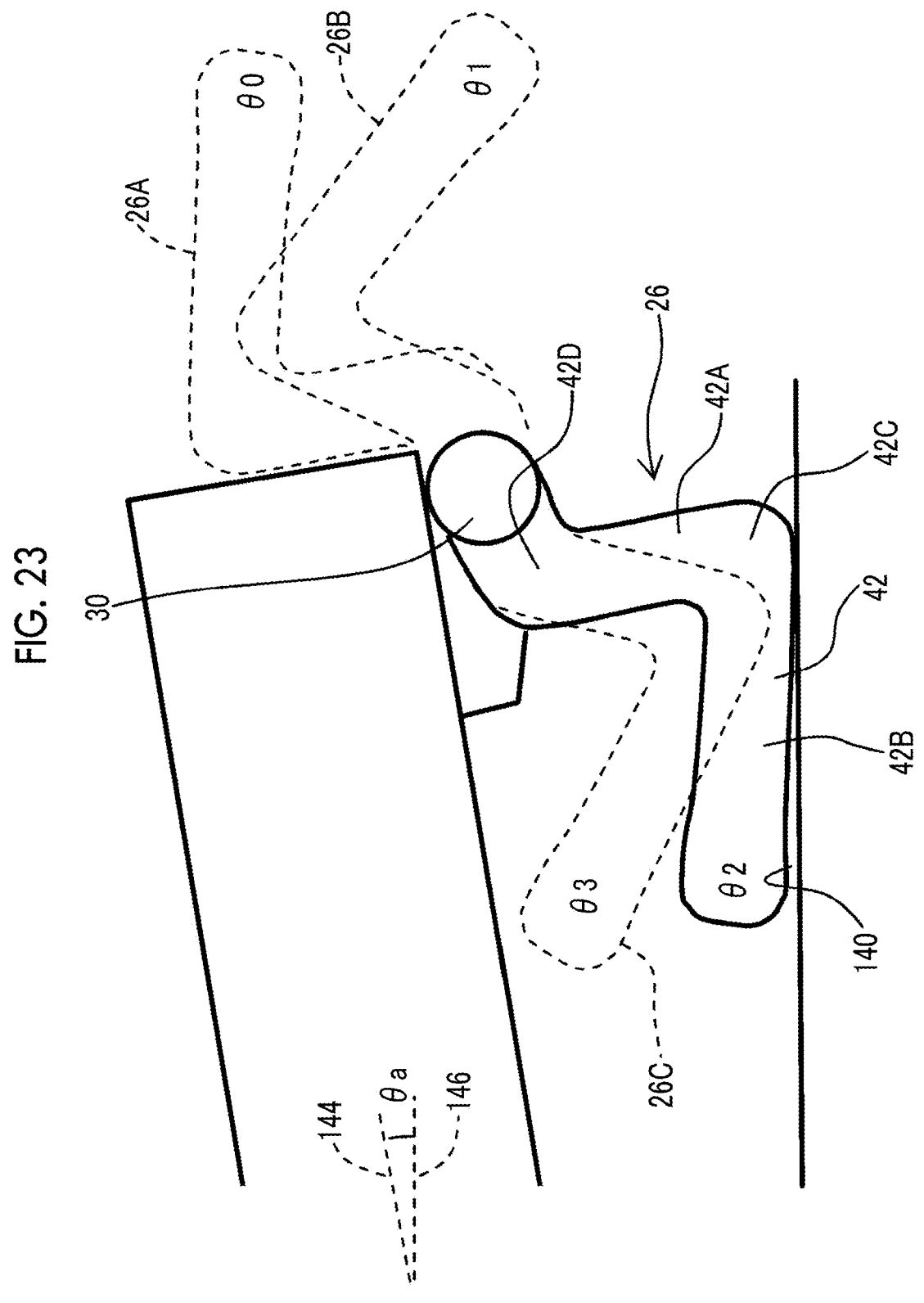
FIG. 23 is a view showing a plurality of postures (rotation angles) that can be taken by a handle.

FIG. 23 shows the handle 26 having a stand posture. The rotation angle of the handle 26 is a second rotation angle θ2. FIG. 23 shows the second arm 42 in the handle 26. The second arm 42 has a first portion 42A that is connected to the hinge mechanism 30, a second portion 42B that is connected to the grip, and a bent portion 42C between the first portion 42A and the second portion 42B. A lower surface (specifically, a pad) of the bent portion 42C is in contact with the table surface. The same applies to the first arm.

In a case where the handle 26 is used as a stand, the grip does not come into contact with the table surface. A gap 140 is present between the grip and the table surface. In each arm, the second portion extends forward from the bent portion, and the entire two arms are accommodated in the lower space of the main body.

Reference numeral 26A indicates a handle during transport. A first rotation angle θ0 is 0 degrees. Reference numeral 26B indicates a handle in a case of fixing the handle. An intermediate rotation angle θ1 is, for example, within a range of 30 degrees to 60 degrees. The second rotation angle θ2 is, for example, 180 degrees. A maximum rotation angle θ3 is, for example, 230 degrees. A handle rotated to the maximum rotation angle θ3 is denoted by reference numeral 26C. The handle is locked for rotation at the first rotation angle θ0 and the second rotation angle θ2 by the handle locking mechanism. In a case where the rotation angle of the handle 26 is the first rotation angle θ0 and the handle 26 is locked, two first portions of the handle are near the rear surface. The two first portions each have a bent form.

Reference numeral 146 indicates a horizontal line, and reference numeral 144 indicates the central axis of the main body. An inclined angle θa of a central axis 144 with respect to a horizon line 146 is, for example, within a range of 8 to 12 degrees. The inclined angle θa of the main body in a case where the handle 26 is used as a stand is the same as the inclined angle of the main body on the cart.

In a case where the handle 26 is used as a stand, the handle 26 is locked at the second rotation angle θ2, so that the posture of the main body unit is stabilized. In addition, since the grip does not come into contact with the table surface as described above, the grip is hygienic. Further, since the handle does not protrude to the rear side of the main body, an advantage in which the handle does not interfere can be obtained.

Figure 24:
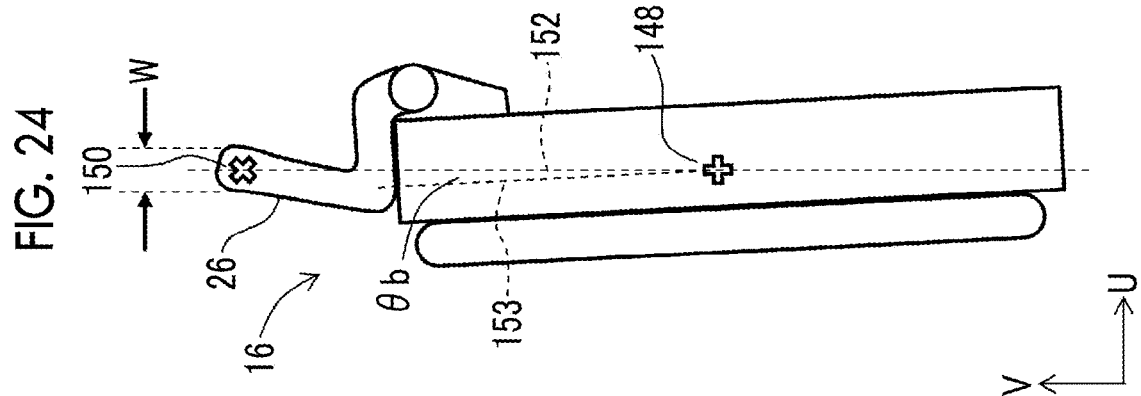
FIG. 24 is a view showing a suspended state of the main body unit.

FIG. 24 shows a state of the main body unit 16 during transport. The main body unit 16 has centroid 148. Reference numeral 152 indicates a vertical line passing through the centroid 148. A vertical line 152 passes through a center 150 of the grip. Reference numeral 153 indicates a line (unit center line) that is an axis parallel to the central axis of the main body and that passes through the centroid 148. The vertical line 152 passes through a width W of the grip. An inclined angle of the unit center line 153 with respect to the vertical line 152 is considerably small, for example, smaller than 2 degrees or 4 degrees.

The main body unit 16 is transported while being suspended. In this case, since the handle 26 is locked at the first rotation angle and an inclined angle θb of the main body unit 16 with respect to the vertical line 152 is considerably small, a risk of the main body unit 16 coming into contact with or colliding with another thing (including the user) can be reduced.

Figure 25:
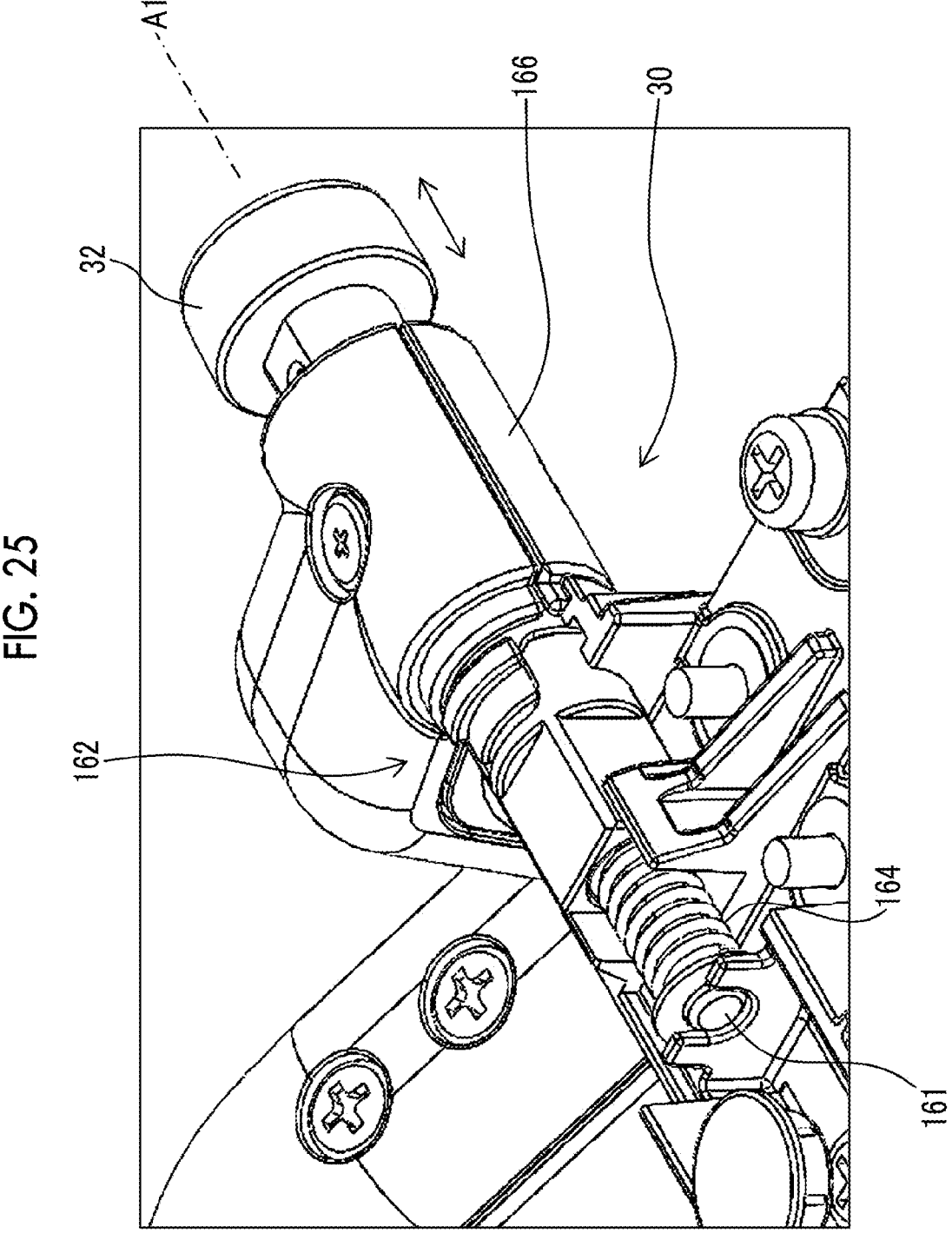
FIG. 25 is a view showing a specific example of a hinge mechanism.

FIG. 25 shows a part of the hinge mechanism 30. The hinge mechanism 30 has a hinge 161, a handle locking mechanism 162, the knob 32, and the like. The hinge 161 has a bearing. The handle locking mechanism 162 has a plurality of cam plates. An elastic force is applied to the knob 32 in a protruding direction. In a case where the knob 32 is pushed, the handle lock is temporarily released. Reference numeral 166 indicates a connecting portion of the arm. Various mechanisms can be adopted as the hinge mechanism 30.

What is claimed is:

1. An ultrasonic diagnostic device comprising:
a main body unit that has a main body which generates an ultrasound image and a display which displays the ultrasound image;
a hinge mechanism that is provided at the main body; and
a handle that has two arms which are connected to the hinge mechanism and a grip which is connected to the two arms,
wherein the hinge mechanism includes a handle locking mechanism that locks the handle at a first rotation angle in a case where the main body unit is transported by gripping the grip;
wherein the hinge mechanism is provided at a rear end part of the main body,
each of the two arms has:
a first portion that is connected to the hinge mechanism, a second portion that is connected to the grip, and
a bent portion between the first portion and the second portion, and
in a case where a rotation angle of the handle is the first rotation angle, the two first portions of the two arms are near or come into contact with a rear surface of the main body;
wherein the handle locking mechanism locks the handle at a second rotation angle different from the first rotation angle in a case where the handle is used as a stand, and
in a case where the handle is used as the stand, the grip is positioned in front of the two bent portions of the two arms;
wherein in a case where the handle issued as the stand, the two bent portions come into contact with a placement surface on which the main body unit is placed, and a gap is generated between the grip and the placement surface.

2. The ultrasonic diagnostic device according to claim 1, wherein the handle locking mechanism locks the handle at a second rotation angle different from the first rotation angle in a case where the handle is used as a stand.

3. The ultrasonic diagnostic device according to claim 2, wherein each of the two arms has a bent portion, and
the second rotation angle is an angle at which the two bent portions of the two arms come into contact with a placement surface on which the main body unit is placed and the grip is separated apart from the placement surface.

4. The ultrasonic diagnostic device according to claim 1, wherein the main body unit has centroid, and
in a case where the main body unit is suspended by gripping the grip, a vertical line passing through the centroid passes through an inside of the grip.

5. The ultrasonic diagnostic device according to claim 1, wherein the handle locking mechanism has a knob that is operated by a user in a case of unlocking the rotation angle.

* * * * *